(12) United States Patent
Abdelghani et al.

(10) Patent No.: US 9,563,740 B2
(45) Date of Patent: Feb. 7, 2017

(54) NEURAL INTERFACE ACTIVITY SIMULATOR

(71) Applicant: The Florida International University Board of Trustees, Miami, FL (US)

(72) Inventors: Mohamed Abdelghani, Miami Beach, FL (US); Ranu Jung, Miami Beach, FL (US); James J. Abbas, Scottsdale, AZ (US); Kenneth Horch, Fountain Hall, AZ (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 14/385,905

(22) PCT Filed: Oct. 16, 2013

(86) PCT No.: PCT/US2013/065205
§ 371 (c)(1),
(2) Date: Sep. 17, 2014

(87) PCT Pub. No.: WO2014/107213
PCT Pub. Date: Jul. 10, 2014

(65) Prior Publication Data
US 2015/0213191 A1     Jul. 30, 2015

Related U.S. Application Data

(60) Provisional application No. 61/714,578, filed on Oct. 16, 2012.

(51) Int. Cl.
G06F 7/60     (2006.01)
G06F 17/10     (2006.01)
(Continued)

(52) U.S. Cl.
CPC .......... *G06F 19/12* (2013.01); *A61B 5/04001* (2013.01); *A61B 5/7203* (2013.01); *G06F 17/10* (2013.01);
(Continued)

(58) Field of Classification Search
CPC ............. G06F 17/5018; G06F 17/5036; G06F 17/5009; G06F 2217/16; G05B 17/02
(Continued)

(56) References Cited

U.S. PATENT DOCUMENTS 5,037,376 A * 8/1991 Richmond ......... A61N 1/36046
128/897
6,440,090 B1 8/2002 Schallhorn et al.
(Continued)

OTHER PUBLICATIONS

Allison, T., et al. "The relationship between human long-latency somatosensory evoked potentials recorded from the cortical surface and from the scalp," *Electroencephalogr Clin Neurophysiol*, 1992, 84(4):301-314.
(Continued)

*Primary Examiner* — Saif Alhija
(74) *Attorney, Agent, or Firm* — Saliwanchik, Lloyd & Eisenschenk

(57) ABSTRACT

Systems and methods to simulate activity that would be recorded using an interface to nerve fibers are provided. Signals, such as motor intent signals, can be converted to neural recordings, such as neural recordings by longitudinal intrafascicular electrodes (LIFEs). Spinal cord motor pools and neural interfaces can be jointly simulated. Realistic simulated neural recordings, such as from electrodes such as LIFEs, can be provided and can be used for the evaluation of decoding algorithms. Systems and methods described herein provide a framework for developing neural interface devices.

21 Claims, 24 Drawing Sheets

(51) Int. Cl.
    G06F 19/12      (2011.01)
    A61B 5/00       (2006.01)
    A61B 5/04       (2006.01)
    G09B 23/28      (2006.01)
    G09B 23/30      (2006.01)
    A61B 5/0488     (2006.01)
(52) U.S. Cl.
    CPC .............. *G09B 23/28* (2013.01); *G09B 23/30*
        (2013.01); *A61B 5/0488* (2013.01); *A61B*
        *5/726* (2013.01); *A61B 5/7264* (2013.01)
(58) Field of Classification Search
    USPC ........................................................... 703/2
    See application file for complete search history.

(56)                References Cited

U.S. PATENT DOCUMENTS

| | | | |
|---|---|---|---|
| 8,160,696 | B2 | 4/2012 | Bendett et al. |
| 2007/0005348 | A1 | 1/2007 | Klefenz |
| 2007/0067003 | A1 | 3/2007 | Sanchez et al. |
| 2007/0194727 | A1* | 8/2007 | McKinstry ............ G05B 13/026 318/53 |
| 2010/0114190 | A1* | 5/2010 | Bendett ............... A61N 1/36014 607/3 |
| 2011/0021943 | A1* | 1/2011 | Lacour ................. A61N 1/0551 600/546 |
| 2011/0125216 | A1 | 5/2011 | Kilgore et al. |

OTHER PUBLICATIONS

Ayaz, H., et al. "An optical brain computer interface for environmental control," *Conf Proc IEEE Eng Med Biol Soc*, 2011, p. 6327-6330.
Bashor, D. P. "A large-scale model of some spinal reflex circuits," *Biological Cybernetics*, 1998, 78(2):147-157.
Blakely, T., et al. "Robust, long-term control of an electrocorticographic brain-computer interface with fixed parameters," *Neurosurg Focus*, 2009, 27(1):E13.
Branner, A., et al. "A multielectrode array for intrafascicular recording and stimulation in sciatic nerve of cats," *Brain Research Bulletin*, 2000, 51(4):293-306.
Capaday, C. "A method for simulating the reflex output of a motoneuron pool," *J Neurosci Methods*, 1987, 21(2-4):91-104.
Carp, J. S. et al., "Motor Neurons and Spinal Control of Movement," *eLS*, 2001, John Wiley & Sons, Ltd.
Cisi, R. R. et al., "Simulation system of spinal cord motor nuclei and associated nerves and muscles, in a Web-based architecture," *J Comput Neurosci*, 2008, 25(3):520-542.
Clark, G. A., et al., "Recording sensory and motor information from peripheral nerves with Utah Slanted Electrode Arrays," *Conf Proc IEEE Eng Med Biol Soc*, 2011, p. 4641-4644.
Dhillon, G. S. et al., "Direct neural sensory feedback and control of a prosthetic arm," *IEEE Trans Neural Syst Rehabil Eng*, 2005, 13(4):468-472.
Dhillon, G. S., et al. "Residual function in peripheral nerve stumps of amputees: Implications for neural control of artificial limbs," *Journal of Hand Surgery-American*, 2004, 29A(4):605-615.
Donoghue, J. P. "Connecting cortex to machines: recent advances in brain interfaces," *Nature Neuroscience*, 2002, 5:1085-1088.
Doud, A. J., et al. "Continuous three-dimensional control of a virtual helicopter using a motor imagery based brain-computer interface," *PLoS One*, 2011, 6(10):e26322.
Duran, C., et al. "AutoSNPdb: an annotated single nucleotide polymorphism database for crop plants," *Nucleic Acids Res*, 2009, 37:(Database issue):D951-953.
Durand, D. M., et al. "Localization and control of activity in peripheral nerves," *Conf Proc IEEE Eng Med Biol Soc*, 2008, p. 3352-3354.

Fok, S., et al. "An EEG-based brain computer interface for rehabilitation and restoration of hand control following stroke using ipsilateral cortical physiology," *Conf Proc IEEE Eng Med Biol Soc*, 2011, p. 6277-6280.
Fraser, G. W., et al., "Control of a brain-computer interface without spike sorting," *J Neural Eng*, 2009, 6(5):055004.
Halder, S., et al. "Neural mechanisms of brain-computer interface control," *Neuroimage*, 2011, 55(4):1779-1790.
Hallin, R. G. "Microneurography in relation to intraneural topography: somatotopic organisation of median nerve fascicles in humans," *J Neurol Neurosurg Psychiatry*, 1990, 53(9):736-744.
Hochberg, L. R., et al., "Reach and grasp by people with tetraplegia using a neurally controlled robotic arm," *Nature*, 2012, 485(7398):372-375.
Hochberg, L. R., et al., "Neuronal ensemble control of prosthetic devices by a human with tetraplegia," *Nature*, 2006, 442(7099):164-171.
Hoffer, J. A. et al., "Implantable electrical and mechanical interfaces with nerve and muscle," *Ann Biomed Eng*, 1980, 8(4-6):351-360.
Huang, D., et al., "Electroencephalography (EEG)-based brain-computer interface (BCI): a 2-D virtual wheelchair control based on event-related desynchronization/synchronization and state control," *IEEE Trans Neural Syst Rehabil Eng*, 2012, 20(3):379-388.
Ivashko, D. G., et at. "Modeling the spinal cord neural circuitry controlling cat hindlimb movement during locomotion," *Neurocomputing*, 2003, 52-4:621-629.
Jankowska, E. "Interneuronal Relay in Spinal Pathways from Proprioceptors," *Progress in Neurobiology*, 1992, 38(4):335-378.
Kamavuako, E. N., et al., "A criterion for signal-based selection of wavelets for denoising intrafascicular nerve recordings," *J Neurosci Methods*, 2010, 186(2):274-280.
Khokhar, Z. O. et al. "Surface EMG pattern recognition for real-time control of a wrist exoskeleton," *Biomed Eng Online*, 2010, 9:41.
Kreilinger, A., et al., "Switching between Manual Control and Brain-Computer Interface Using Long Term and Short Term Quality Measures," *Front Neurosci*, 2011, 5:147.
Krusienski, D. J. et al., "Control of a brain-computer interface using stereotactic depth electrodes in and adjacent to the hippocampus," *J Neural Eng*, 2011, 8(2):025006.
Kuiken, T. A, et al. "Targeted muscle reinnervation for real-time myoelectric control of multifunction artificial arms," *JAMA*, 2009, 301(6):619-628.
Lawrence, S. M., et al. "Acute peripheral nerve recording characteristics of polymer-based longitudinal intrafascicular electrodes," *IEEE Transactions on Neural Systems and Rehabilitation Engineering*, 2004, 12(3):345-348.
Lefurge, T., et al., "Chronically implanted intrafascicular recording electrodes," *Ann Biomed Eng*, 1991, 19(2):197-207.
Long, J., et al., "A hybrid brain computer interface to control the direction and speed of a simulated or real wheelchair," *IEEE Trans Neural Syst Rehabil Eng*, 2012, 20(5):720-729.
Lowery, M. M. et al., "A simulation study to examine the effect of common motoneuron inputs on correlated patterns of motor unit discharge," *Journal of Computational Neuroscience*, 2005, 19(2):107-124.
Malagodi, M. S., et al. "An intrafascicular electrode for recording of action potentials in peripheral nerves," *Ann Biomed Eng*, 1989, 17(4):397-410.
McKhann, G. M. 2nd, "Cortical control of a prosthetic arm for self-feeding," *Neurosurgery*, 2008, 63(2):N8-9.
Micera, S., et al., "Decoding of grasping information from neural signals recorded using peripheral intrafascicular interfaces," *J Neuroeng Rehabil*, 2011, 8:53.
Micera, S., et al., "On the use of longitudinal intrafascicular peripheral interfaces for the control of cybernetic hand prostheses in amputees," *IEEE Trans Neural Syst Rehabil Eng*, 2008, 16(5):453-472.
Nussbaumer, R. M., et al. "Computer simulation of the motoneuron pool-muscle complex. I. Input system and motoneuron pool," *Biological Cybernetics*, 2002, 86(4):317-333.
Onose, G., et al. "On the feasibility of using motor imagery EEG-based brain-computer interface in chronic tetraplegics for

(56) References Cited

OTHER PUBLICATIONS assistive robotic arm control: a clinical test and long-term post-trial follow-up," *Spinal Cord*, 2012, 50(8):599-608.

Polikov, V. S., et al., "Response of brain tissue to chronically implanted neural electrodes," *J Neruosci Methods*, 2005, 148(1):1-18.

Qiao, S., et al., "Stationary wavelet transform and higher order statistical analyses of intrafascicular nerve recordings," *J Neural Eng*, 2012, 9(5):056014.

Rehbaum, H., et al., "Real time simultaneous and proportional control of multiple degrees of freedom from surface EMG: Preliminary results on subjects with limb deficiency," *Conf Proc IEEE Eng Med Biol Soc*, 2012, p. 1346-1349.

Stienen, A. H., et al., "Analysis of reflex modulation with a biologically realistic neural network," *J Comput Neurosci*, 2007, 23(3):333-348.

Subramanian, K., et al., "NVIZ: An integrated environment for simulation, visualization and analysis of spinal neuronal dynamics," *Journal of Imaging Science and Technology*, 2005, 49(5):505-519.

Tang, Y., et al. "An algorithm for source signal extraction from the peripheral nerve," *Conf Proc IEEE Eng Med Biol Soc*, 2011, p. 4251-4254.

Tyler, D. J. et al., "Functionally selective peripheral nerve stimulation with a flat interface nerve electrode," *IEEE Trans Neural Syst Rehabil Eng*, 2002, 10(4):294-303.

Uchiyama, T. et al., "Effects of spinal recurrent inhibition on motoneuron short-term synchronization," *Biological Cybernetics*, 2007, 96(6):561-575.

Velliste, M., et al. "Cortical control of a prosthetic arm for self-feeding," *Nature*, 2008, 453(7198):1098-1101.

Veraart, C., et al., "Selective control of muscle activation with a multipolar nerve cuff electrode," *IEEE Trans Biomed Eng*, 1993, 40(7):640-653.

Wang, P. T., et al. "Self-paced brain-computer interface control of ambulation in a virtual reality environment," *J Neural Eng*, 2012, 9(5):056016.

Wodlinger, B. "Extracting Command Signals from Peripheral Nerve Recordings," *Doctor of Philosophy*, 2011, Case Western Reserve University.

Wodlinger, B. et al., "Recovery of neural activity from nerve cuff electrodes," *Conf Proc IEEE Eng Med Biol Soc*, 2011, p. 4653-4656.

Wolpaw, J. R., et al., "An EEG-based brain-computer interface for cursor control," *Electroencephalogr Clin Neurophysiol*, 1991, 78(3):252-259.

Wood, F., et al., "Automatic spike sorting for neural decoding," *Conf Proc IEEE Eng Med Biol Soc*, 2004, 6:4009-4012.

Yoshida, K., et al., "Development of the thin-film longitudinal intra-fascicular electrode," *Proceedings of the fifth Annual Conf. of the IFESS*, 2000.

Zhou, R., et al., "A computational model and simulation study of the efferent activity in the brachial nerves during voluntary motor intent," *Med Biol Eng Comput*, 2010, 48(1):67-77.

Zhu, X., et al., "Bayesian Method for Continuous Cursor Control in EEG-Based Brain-Computer Interface," *Conf Proc IEEE Eng Med Biol Soc*, 2005, 7:7052-7055.

\* cited by examiner

NEURAL INTERFACE ACTIVITY SIMULATOR

CROSS-REFERENCE TO RELATED APPLICATIONS

This application is a National Stage Application of International Application Number PCT/US2013/065205, filed Oct. 16, 2013, which claims the benefit of U.S. provisional application Ser. No. 61/714,578, filed Oct. 16, 2012, the disclosures of which are incorporated herein by reference in their entireties, including all figures and tables.

This invention was made with government support under a grant awarded from the Defense Advanced Research Projects Agency (DARPA) under grant number N66001-12-C-4195. The government has certain rights in this invention.

BACKGROUND OF INVENTION

Many spinal cord simulators are designed for a particular goal and emphasize a specific detail of spinal cord physiology. For example, anatomical aspects of the cat spinal cord are sometimes emphasized while neuronal and synaptic physiology for human electrophysiology can also be focused on. However, existing simulators require large computational resources and long simulation times and use complex computational models that are primarily useful for studying specific physiologic behavior, such as H-relfex or simple one- or two-joint walking.

BRIEF SUMMARY

Embodiments of the subject invention provide systems and methods to simulate activity that would be recorded using an interface to nerve fibers (e.g., nerve fibers of a human subject). Such activity includes, but is not limited to, neural activity. Such systems and methods can act as a neural interfaces simulator. For example, systems and methods of the subject invention can convert motor intent signals to neural recordings (e.g., by longitudinal intrafascicular electrodes (LIFEs)). Systems and method of the subject invention can assist in decoding motor intent for the control of neural prostheses by neural signals. Advantageously, spinal cord motor pools and neural interfaces can be jointly simulated. Systems and method of the subject invention can provide realistic simulated neural recordings (e.g., from electrodes such as LIFEs), which can be used for, e.g., the evaluation of decoding algorithms. Systems and methods of the subject invention can provide a framework for developing neural interface devices.

In one embodiment, a system includes a computer-readable medium having computer-executable instructions for performing a method to simulate activity recorded from an interface to nerve fibers. The method includes simulating generation of at least one signal of a variable capable of being recorded by an interface to nerve fibers; simulating translation of the variable to motor neuron firing; and simulating recording of the motor neuron firing by the interface to nerve fibers. In a particular embodiment, the variable is motor intent.

In another embodiment, a method of simulating activity recorded from an interface to nerve fibers includes: simulating, by a system comprising a computer-readable medium, generation of at least one signal of a variable capable of being recorded by an interface to nerve fibers; simulating translation of the variable to motor neuron firing; and simulating recording of the motor neuron firing by the interface to nerve fibers. In a particular embodiment, the variable is motor intent.

DETAILED DISCLOSURE

Figure 1:
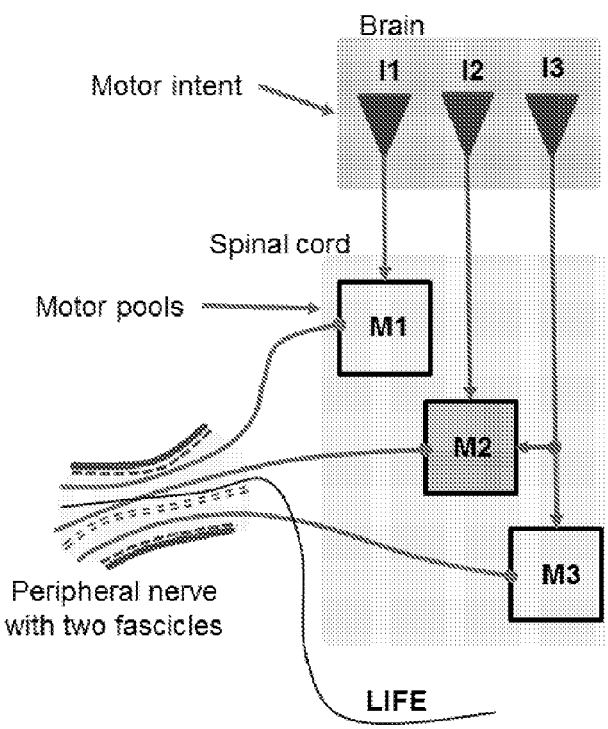
FIG. 1 shows a diagram of a motor control system according to an embodiment of the subject invention.

Embodiments of the subject invention provide systems and methods to simulate activity that would be recorded using an interface to nerve fibers (e.g., nerve fibers of a human subject). Such activity includes, but is not limited to, neural activity. Such systems and methods can act as a neural interfaces simulator. For example, systems and methods of the subject invention can convert motor intent signals to neural recordings (e.g., by longitudinal intrafascicular electrodes (LIFEs)). Systems and method of the subject invention can assist in decoding motor intent for the control of neural prostheses by neural signals. Advantageously, spinal cord motor pools and neural interfaces can be jointly simulated. Systems and method of the subject invention can provide realistic simulated neural recordings (e.g., from electrodes such as LIFEs), which can be used for, e.g., the evaluation of decoding algorithms. Systems and methods of the subject invention can advantageously provide a framework for developing neural interface devices. Though the simulated activity is neural activity in many of the embodiments disclosed throughout this description, this is by way of example only and it should be understood that the simulated activity can be any activity that can be recorded using an interface to nerve fibers (e.g., nerve fibers of a human subject).

Systems and methods of the subject invention can be used to map a variable in order to simulate firing of nerve fibers. The mapped variable can be, for example, motor intent, hormonal level(s), or autonomic drive, though embodiments are not limited thereto. Thus, the input can be concrete (e.g., hormonal level) or more abstract (e.g., motor intent). Though motor intent is mentioned as an input variable many times throughout this description, this is by way of example only and it should be understood that other input variables can be used, including but not limited to hormonal level(s) and autonomic device.

Systems and methods of the subject invention can be used to simulate firing of nerve fibers for controlling, e.g., skeletal muscle, smooth muscle, or one or more glands, though embodiments are not limited thereto. The end organ being controlled can be an organ that is typically controlled by neural activity that can otherwise be recorded and for which a transformation map can be made between the input and the output measure (e.g., neural firing frequency). Though skeletal muscle is discussed as the end organ many times throughout this description, this is by way of example only and it should be understood that other end organs can be used, including but not limited to smooth muscle and one or more glands. In an embodiment, a system can include one or more of: a motor intent generation unit; a motor pools unit; and an electrode function unit. In many embodiments, all three of these elements are present. Many of the functions used in the simulator can be linear transformations. A linear transformation can describe the connectivity between upper motor neurons, which can be used as sources of motor intent signals, and spinal cord motor neurons. Also, a linear function can describe which electrode will record from what axons. One nonlinear transformation can be involved and can help determine how motor neurons translate motor intent signals to neural firings. A system of the subject invention can advantageously have a simple design, which is essentially linear, to cut down on simulation time and make the code easily scalable. The simulator is effective in generating a large amount of simulated neural data for testing of decoding methods.

As used herein, and unless otherwise specifically stated, the terms "operable communication" and "operably connected" mean that the particular elements are connected in such a way that they cooperate to achieve their intended function or functions. The "connection" may be direct or indirect, physical (e.g., by wires or other physical connections) or remote (e.g., wireless).

Though spinal cord simulators are designed for a particular goal and emphasize a specific detail of spinal cord physiology, many embodiments of the subject invention focus on the overall function of the central nervous system and spinal cord motor neurons in order to translate intended movement to firing patterns. Systems and methods of the subject invention also focus on: the function of neural-interfaces and the way they record resulting neural signals; generating large neural data sets for a multitude of possible scenarios such as multiple degrees of freedom movements, placement and geometry of recording electrodes, degree of encapsulation, multiple spikes shapes, crosstalk, etc.; rapid prototyping of decoding algorithms; and scalability and speed of processing.

In one embodiment, a system or method simulates LIFE recordings. With such a LIFE simulator, realistic electrode recordings can be simulated with different combinations of motor pool involvement. Also, neural recordings from multiple LIFEs can be simulated for multi-degree of freedom (DOF) tasks, data with different spike morphologies can be simulated, and special effects such as superposition of spikes can be tested.

In many embodiments, a mathematical model is used to simulate motor intent, motor neurons, and/or neural interfaces. The mathematical models of the subject invention are computationally simple yet efficient and effective.

In one embodiment, a graphical user interface (GUI) is used to assist a user with tasks involved in the simulation, including but not limited to configuring the simulator parameters and displaying results.

In a particular embodiment, a finite element model (FEM) for neural interfaces can be coupled to the simulator. In a further embodiment, indirect movement control pathways can be simulated. In yet a further embodiment, sensory feedback pathways from external devices can be used in conjunction with and/or as part of a system or method of the subject invention.

It is possible, using recordings with LIFEs from peripheral nerve stumps in amputees, to control a one-DOF robotic arm in a graded fashion (Dhillon, Lawrence et al. 2004; Dhillon and Horch 2005). However, to develop efficient decoding algorithms, it is desirable to use computer models of the peripheral neuro-muscular system to explore a greater range of approaches than can be readily done in animal models. Systems and methods of the subject invention can model and simulate motor pools (e.g., spinal cord motor pools) and recordings (e.g., by electrodes such as LIFEs) from subpopulations of motor axons. Related art simulators do not consider neural interfaces at all and focus on simulation of spinal cord motor nuclei and associated muscles.

For example, a recent simulator developed by Cisi et al. (Cisi and Kohn 2008) is a web-based simulation system of the spinal cord circuitry and muscles it controls, and this simulator requires a large amount of computational resources.

In many embodiments, a simulator can produce simulated recordings from multiple LIFEs for multi-DOF tasks with known motor intents, spike train characteristics, levels of encapsulation, and signal-to-noise ratios (SNRs). Such a simulator enables comprehensive comparison of candidate algorithms and assesses capability to decode recordings in various conditions, such as those with a high degree of spike overlap.

Systems and methods of the subject invention can receive input from any suitable source, including any type of electrodes. Electrodes that can be used with the subject invention include, but are not limited to, CUFF, Utah Slanted Electrode Array (USEA), flat interface nerve electrode (FINE), longitudinal intrafascicular electrode (LIFE), tfLIFE (thin film LIFE), and penetrating arrays. Though LIFEs are used in many embodiments and examples, this is by way of example only and it is to be understood that other types of electrodes can be used.

Motor intent is voluntary neuromuscular system activity generated to attain some goal. For example, motor intent can be an attempt to flex the biceps, extend the wrist, or reach and grasp an object. Motor intent is formulated in the brain and descends to the spinal cord motor pools on several descending motor pathways.

In many embodiments, motor intent within a model is defined as effort(s) to stabilize and control a single joint or coupled sets of joints. That is, motor intent can involve two essential aspects, intended action and level of effort. Intended action is what is being controlled while intended effort is the desired amount of force to be generated in the involved muscles. A motor intent vector is the set of the components of a particular motor intent.

In an embodiment, descending pathways are modeled functionally. The connectivity between descending motor tracks and motor neurons is modeled by a linear mapping matrix. Motor intent signals are programmed into the simulator as analog signals and directly activate motor neurons to produce firing patterns.

FIG. 1 shows a diagram of a motor control system, which can be simulated by systems and methods of the subject invention. Referring to FIG. 1, motor intent is generated in the brain and descends in spinal cord tracks to spinal cord motor pools. Motor pools in the spinal cord translate motor intent to firing patterns in motor neurons. Axons from motor pools in the spinal cord travel in groups through peripheral nerves. A peripheral neural interface (e.g., LIFE electrodes) accesses signals carried on motor axons at the level of the peripheral nervous system. In an embodiment, a system simulates this process in generation of motor intent signals, translation of motor intents to motor neuron firing, and recording of this neural activity by peripheral nerve interface electrodes. In FIG. 1, I represents collected brain activity corresponding to a particular motor intent, and M represents a motor pool associated with a particular muscle.

A motor pool is a group of motor neurons that innervate a single muscle and is responsible for the control of a single direction of movement. Motor neurons integrate sensory and higher central inputs and issue firing patterns to muscle fibers. A motor neuron can innervate multiple fibers in a single muscle. There are three main classes of motor neurons: alpha motor neurons control skeletal muscles leading to movement; gamma motor neurons control sensitivity of muscle spindles to stretch thereby modulating contraction strength; and beta motor neurons can do either. Alpha motor neurons fall into three subclasses according to the contractile properties of the muscle fibers they innervate: fast-twitch fatigable (FF); fast-twitch fatigue-resistant (FR); and slow-twitch fatigue-resistant (S). The functionality of a motor pool is determined not only by the motor neuron classes but also by their recruitment characteristics. The recruitment of motor neurons in a motor pool is postulated to follow the size principle; that is, small motor neurons fire first and as excitatory inputs increase larger motor neurons are recruited and contraction strength increases. Small motor neurons connect to slow fibers while larger ones innervate fast twitch fiber. In many embodiments, motor neurons can be modeled as FF, FR or S and then grouped in a recruitment class based on the size principle. In a particular embodiment, the characteristics of motor neurons can be set using parameter files.

Peripheral nerves carry information from and to central nervous system via efferent and afferent axons, respectively. They are somatotopically organized even at fascicular and subfascicular level, so motor neurons innervating a particular muscle tend to run together for the entire length of their path in a peripheral nerve. For control of the hand, the most relevant peripheral nerve branches are median nerve (MN), ulnar nerve (UN), and radial nerve (RN), which govern six wrist and hand motions: hand closing (HC); hand opening (HO); wrist flexion (WF); wrist extension (WE); wrist pronation (WP); and wrist supination (WS). Table 1 shows nerves that control different joint movements. The map between nerves and actuation direction is that of many-to-many. However, the mapping of motor pools is more specific in the sense that one motor pool controls one muscle. The placement of a LIFE electrode is typically within a group of motor axons associated with the same motor pool and hence will record signals corresponding to one direction of actuation. In one embodiment of the subject invention, the organization of peripheral nerves is tied to the grouping of motor neurons into motor pools and can be programmed by the user.

In many embodiments, the peripheral neural interface used with the system or method can be one or more LIFEs. In a particular embodiment, the LIFEs can be fabricated from 25, 50, or 100 µm diameter Teflon® insulated 90% Pt-10% Ir. A 1 mm recording site can be made by removing part of the insulation. A LIFE can be placed in a fascicle parallel to its axons. A system of multiple LIFEs implanted in multiple peripheral nerve fascicles can record from multiple motor pools and achieve greater numbers of different motor actions. In certain embodiments, the placement of LIFEs in peripheral nerves may be semi-random. The knowledge of nerve gross anatomy helps guide the placement of electrodes in the correct nerves corresponding to the actions to be recorded. However, the determination of which fascicle or region in a fascicle the electrode will end up may be difficult; hence, the specific actions it will relate to may also be difficult to determine. The motor activity it detects depends on where the electrode is placed (e.g., in which fascicle and in which part of that fascicle). These unknowns can be determined (decoded) experimentally. Similar decoding procedures have been carried out for cortical and other peripheral interfaces. In many embodiments, placement of multiple LIFEs is determined by their relation to motor axons. This relation is modeled by a motor axon to electrode mapping matrix defined by an input parameter file.

TABLE 1

Nerves that control different joint movements.

| Joint | Movement | Nerve(s) |
|---|---|---|
| MCP IP | Flexion | Median |
|  | Extension | Radial |
|  | Ab/Adduction | Ulnar |
| Thumb | Flexion | Median, Ulnar |
|  | Extension | Median |
|  | Abduction | Radial |
|  | Adduction | Ulnar |
| Wrist | Flexion | Median, Ulnar |
|  | Extension | Radial |
|  | Abduction | Median, Ulnar |
|  | Adduction | Median, Ulnar |
|  | Pronation | Median |
|  | Supination | Radial |

Superposition is the summation of neural signals from multiple sources on a single recording electrode. It depends on the structure and relative position of an electrode with respect to neural sources. For example, a LIFE electrode might record from multiple axons belonging to different motor pools involved in different movements. Superposition has two undesirable effects, crosstalk and superposition of spikes. Crosstalk can occur when a neural electrode picks up neural signals from motor axons emanating from different motor pools. This may lead to superposition of different motor intents on a single electrode recording. Superposition of spikes is a sum of spike waveforms, which can be constructive, resulting in large spikes, or destructive, leading to the failure to detect neural activity. Superposition of spikes can distort spike shapes and alter the apparent firing frequencies in recorded neural activities.

Drift is unwanted relative motion between the neural interface and neural sources. Drift can change recorded firing patterns and crosstalk. Encapsulation is the accumulation of biological matter on the neural interface to a varying amount as a result of physiological responses. Encapsulation attenuates neural signals and can lead to dysfunctional electrodes.

Noise is everywhere, including in the biological tissue, in the neural-tissue interface, in the recording system, and in the environment. Sources of noise in peripheral neural interfaces include: electromyogram (EMG) from muscles in the vicinity of the electrode; electrocardiac signals; background neural activity from motor or sensory axons; tissue thermal noise; thermal and impedance properties of the neural interface; recording system and environmental noise such as power hum; and flicker noise.

Figure 4:
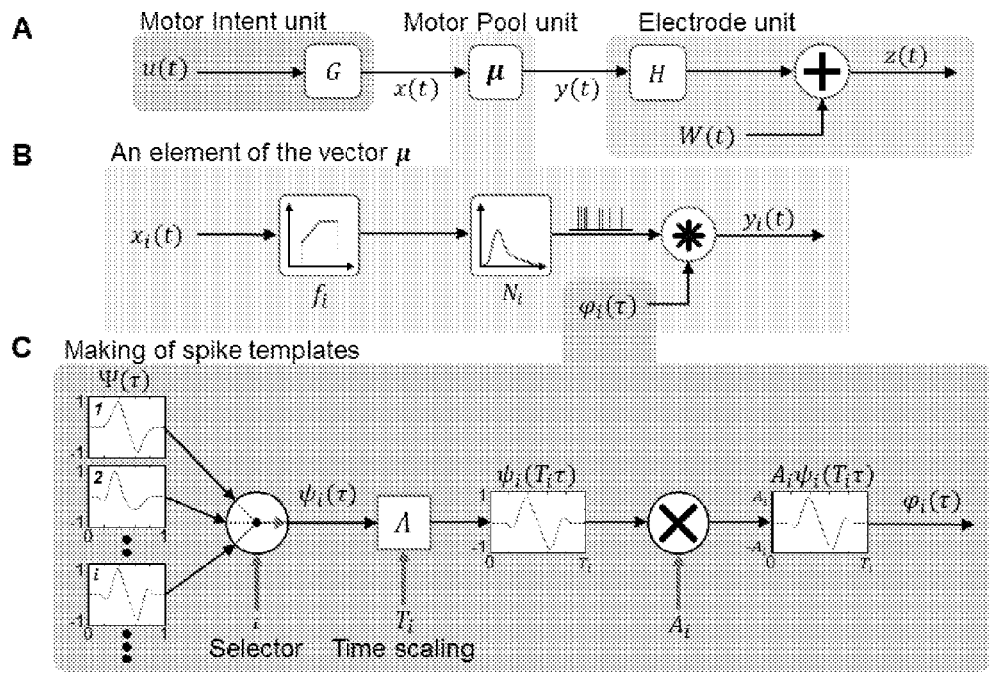
FIGS. 4A-4C show a diagram of a simulator according to an embodiment of the subject invention.

FIG. 4 shows a diagram of a simulator according to an embodiment of the subject invention. Referring to FIG. 4A, descending tracts carry motor intent to motor neurons pools, and this structure can be described by the following model:

$$x(t) = Gu(t) \quad (1)$$

where u is an n×1 vector quantity representing motor intent signals at their lowest control level (i.e., the intention to contract a particular muscle) and n is the number of motor intent signals. The values taken by u are not spikes trains but normalized intended effort (force). G maps motor intent to motor neurons. It is an m×n matrix, with m≥n, where m is the number of spinal cord motor neurons found in motor pools. G represents the connectivity between descending tracts and motor neurons in spinal cord. x is an m×1 vector of the motor neuron activation states. The activation state $x_i(t)$ can be considered as the graded membrane potential just prior to the axon hillock of motor neuron i; it is the signal that would determine the mean firing rate of a motor neuron.

The structure of G describes how cortical descending tracks connect to motor pools of the spinal cord. In an embodiment of the subject invention, the driving inputs from upper motor centers, being carried on descending axons, are referred to as the motor intent vector and the connectivity, the G map, is restricted to direct control of motor pools. In certain embodiments, indirect pathways can be ignored. Also, motor intent signals can be assumed to have analog values, not firing patterns. The conversion of descending firing patterns to analog motor neuron activation state can be done at motor neuron input synaptic levels. This assumes that motor neuron activation state is a faithful representation of the intended effort.

The firing pattern of a motor neuron depends on its input/output response curves, whether the neuron type is S, FR, or FF, and the regularity of firing rate. Let y be the extracellular axon potential at the level of recording site. Referring to FIGS. 4A and 4B, y can be described by the following equation:

$$y(t) = \mu(x(t)). \quad (2)$$

y can also be thought of as the firing of motor neurons. y is an m×1 vector, and μ is a function that maps motor neurons activation state x to y and is defined by the following steps:

First, let $$N(\xi) \sim \begin{cases} \xi \\ \text{Poisson}(\xi) \\ \text{TruncatedGaussian}(\xi, \sigma) \\ \text{Gamma}(\xi, \sigma) \\ \text{Uniform}(\xi, w) \end{cases} \quad (3)$$

be a stochastic point process having either one of the distributions listed above. The activation state x determines the mean interspike interval (ISI) ξ. In an embodiment of the subject invention, the mathematical model can choose any one of the different point processes for spike trains: Identity, Poisson, Truncated-Gaussian, Gamma, or Uniform (Equation 3). Identity produces a regular spike train, which is important for testing simulator functionality. Poisson produces an irregular spike train, where the variability is dependent on the mean firing rate ξ. In the last three processes, the variability in ISI can be set independently of the mean ISI. This is useful for evaluating decoding algorithm performance under different level of ISI variability while the mean ISI remains fixed.

Second, the input/output response curve for motor neurons is given by:

$$f(x) = \begin{cases} 0, & 0 \le x < x_{thr'} \\ f_{slp}x, & x_{thr'} \le x < x_{sat'} \\ f_{sat'} & x \ge x_{sat'} \end{cases} \quad (4)$$

where the slope $f_{slp}$ of the input/output response curve is given by:

$$f_{slp} = \frac{f_{sat} - f_{thr}}{x_{sat} - x_{thr}} \quad (5)$$

where $x_{thr}$ is the threshold activation state above which a motor neuron begins to fire. $f_{thr}$ and $f_{sat}$ are the minimum and maximum frequency of firing for a motor neuron, while $x_{sat}$ is the activation level at which a motor neuron firing rates saturates. The output of the function $f$ is the frequency of firing in Hz. The activation state x is of normalized scale with x=0 zero effort and x=1 maximum effort. $x_{thr}$ determines the recruitment order of the motor neuron. In an embodiment, $x_{thr}$, $f_{thr}$, $x_{sat}$, and $f_{sat}$ can be set by the user for each motor neuron.

Figure 2:
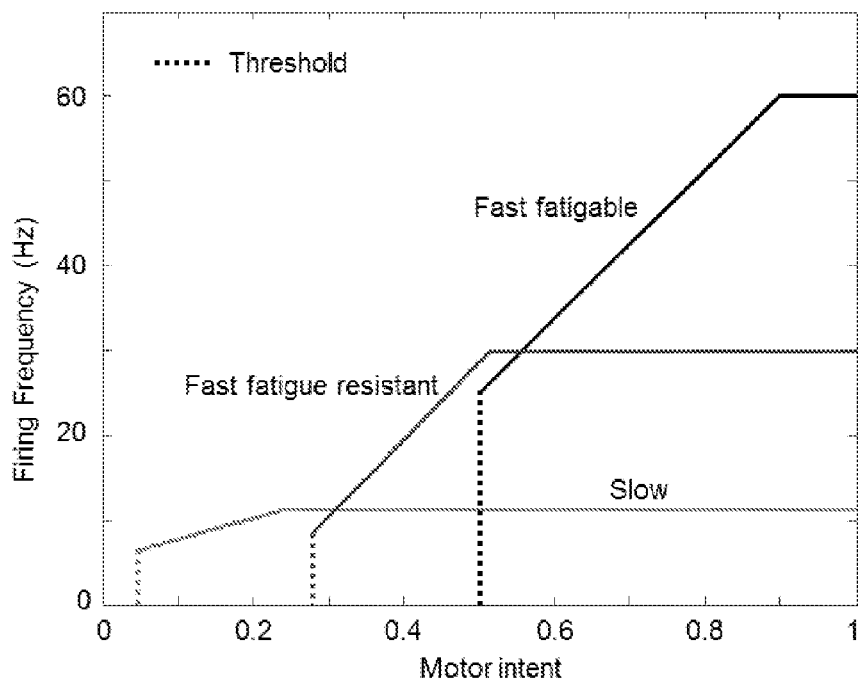
FIG. 2 shows a plot of firing frequency as a function of motor intent.

FIG. 2 shows an input/output response curve for motor neurons in the form of a plot of firing frequency as a function of motor intent.

Each motor neuron has a characteristic spike shape. Important features of spike shapes are their morphology, amplitude, and duration. The shape of the spike is determined by intrinsic and extrinsic factors. Intrinsic factors include the number and type of voltage gated channels, the size of the axon, whether or not it is myelinated, and the general health of axons (e.g., atrophy after amputation changes spike shapes). Extrinsic factors include the recording electrode material type, geometry, location, and orientation with respect to neural sources. This includes the degree and type of encapsulation. Spikes can occupy a frequency bandwidth between, for example, 100 Hz and 10 kHz, depending on the recording electrode (Horch and Dhillon 2004), (Brand 2005), (Lynch and O'Mara 1997). Some common shapes of action potential recorded by various electrodes can be found in the related art (Malagodi, Horch et al. 1989; Lefurge, Goodall et al. 1991; Lawrence, Dhillon et al. 2004; Dhillon and Horch 2005; Micera, Navarro et al. 2008).

Figure 3:
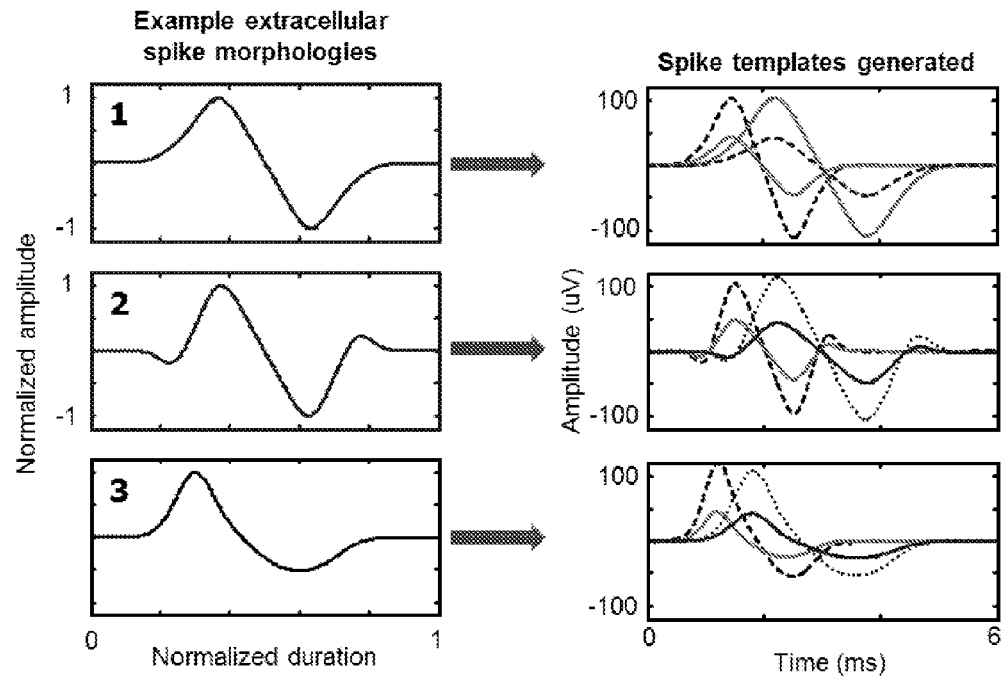
FIG. 3 shows plots of spike templates.

Peripheral neural spikes come in many different shapes, durations, and amplitudes, and no database of experimentally-obtained (by peripheral interfaces) spike templates exists. Accordingly, embodiments of the subject invention also provide processes to simulate probable spike templates. In one embodiment, spike shapes can be programmed by a user of the simulator in several steps. First, the user selects normalized spike morphologies. FIGS. 3 and 4C show an example of such a step. Referring to FIG. 3, three spike morphologies with normalized amplitudes between (−1, 1) and normalized duration between (0, 1) are scaled in time and amplitude to form a multitude of spike templates. A spike template is a characteristic of a neuron. The shape of the spike depends on neuron type, axon size and myelination, shape and distance of the recording electrode from the axon, and degree and type of encapsulation around the electrode. Spike morphologies are classified in terms of the number of peaks and troughs they have and whether they are symmetric or not. Template 1 is symmetric with one peak and one trough, template 2 is symmetric with two peaks and two troughs, and template 3 is asymmetric with one peak and one trough. Other spike morphologies are possible and can be directly programmed in the simulator.

Spike morphologies can be generated by taking derivatives of Gaussian and Gamma functions. These spike wavelets cover many of the current known spike shapes. The spike wavelets have been normalized in amplitudes between (−1, 1) and normalized in duration between (0, 1). Referring to FIG. 4C, in a particular embodiment, the spike-morphologies can then be scaled in amplitude and duration by the simulator using parameters that can be specified by the user.

Let $\Psi(t)$ be an in m×1 vector function that encodes spike shapes of motor neurons. $\phi(t)$ will have the following properties:

$$\int_{-\infty}^{\infty}\psi(s)ds=0, \quad (6)$$

and $$\int_{-\infty}^{\infty}\psi^2(s)ds<\infty. \quad (7)$$

Referring to FIG. 4, spike train generated by a motor neuron can be defined as follows:

$$\mu(x(t))=\int_0^t\psi(t-\tau)dN(f(x(\tau))). \quad (8)$$

If N is a Poisson process, then the function $\mu$ can be rewritten as:

$$\mu(x(t)) = \sum_{i=0}^{\infty}\int_0^t\varphi(t-\tau)\delta(\tau-\tau_{f(x)})d\tau. \quad (9)$$

Referring again to FIG. 4A, in one embodiment, the recording equation is $$z(t)=H(y(t))+W(t) \quad (10)$$

where H is an l×m matrix that maps m motor axons to l electrodes. H depends on where the electrodes are placed in peripheral nerves (e.g., in the median nerve or in the ulnar nerve, inside or outside of a fascicle or cuffed around a nerve). H determines how many motor axons the electrodes are recording from and which motor pools they are in. It also determines the strength of the recorded signals. For example, axons distant from the electrode contribute weakly to the recorded signals. In an embodiment, H can be configured by the user to test different electrode configuration and recording scenarios. For example, a LIFE electrode may pick between 6-10 motor axons signals, a UTAH array may pick from 0-6 motor axons per electrode, and a CUFF may pick a barrage of neural activity from thousands of motor axons. The H map may not be fully known and may need to be estimated by decoding algorithms. However, the electrodes can be in one nerve or another so the group from which motor pools record can be known a priori. Hence, H can be partially known by the placement of electrodes in peripheral nerves.

W is noise, an l×1 vector. It is the sum of all noise sources in the environment. In one embodiment of the simulator, noise is modeled as $1/f^\beta$ power-law noise whose intensity and $\beta$ can be specified by the user. The decoder's job is to estimate the map H and filter out motor intents signals x knowing only z, partial knowledge of H, signal to noise ratios, and the subject's remaining control over motor intents x.

Figure 5:
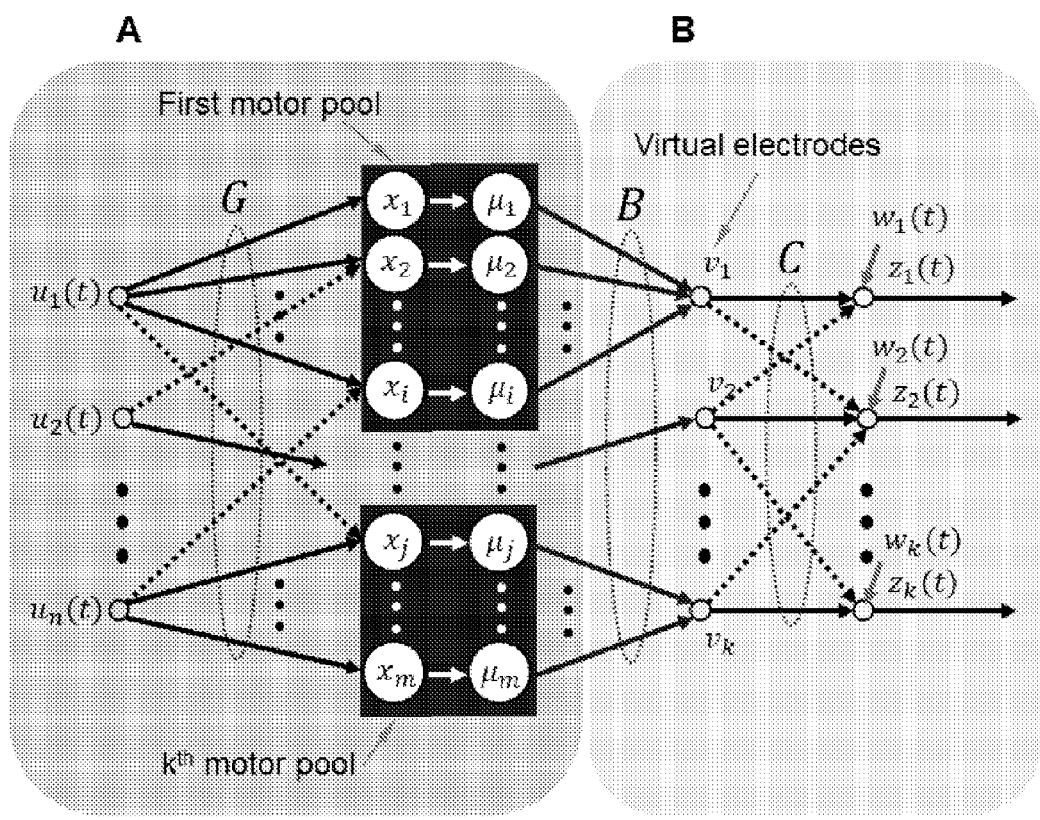
FIGS. 5A-5B show a diagram of a simulator according to an embodiment of the subject invention.

In certain embodiments, to define a recording model for LIFEs, the map H is provided with some structure. FIG. 5 shows a diagram of a simulator according to an embodiment of the subject invention. FIG. 5A is a network flow chart representation for the functionality of the motor intent and motor pool units, and FIG. 5B is a network flow chart representation of the operation of a multiple LIFE electrode recording interface. G is a matrix that transforms motor intent signals to motor neuron activation state x. Motor pools (black boxes) in the spinal cord translate their activation states x to neural firings. The matrix B maps neural firing to virtual electrode signals; virtual electrodes are a conceptual tool to stand for the optimal placement of LIFE electrodes in the peripheral nervous system. The optimal placement of electrodes is such that there is no cross talk between signals recorded on each electrode or that each electrode is recording from one and only one motor pool. C is the cross-talk matrix for when electrodes are in less ideal locations and mixing of signals between motor pools signals appears in recordings. Referring to FIG. 5, H is divided into two matrices B and C. B maps activity from a subset of related motor axons (i.e., the same motor pool) into a set of virtual electrodes v:

$$v(t)=B(y(t)). \quad (11)$$

Therefore, signals detected by the virtual electrodes represent pure motor commands destined to a particular muscle. The mapping matrix C is the degree of crosstalk between motor pools or in this case virtual electrodes. Thus, $$H=CB \quad (12)$$

where H is an l×m matrix, m motor axons and l electrodes, where l≤m suggesting that not all motor pools can be recorded from. C is an l×l matrix. Knowing the structure and function of LIFEs, it can be assumed that C is nearly the Identity matrix. That is, cross-talk between motor pools is negligible. Hence, the LIFEs electrode signal z is given by:

$$z(t)=Cv(t)+W(t). \quad (13)$$

In one embodiment, H can be set as a product of the two matrices CB where each matrix can be configured separately. Further, users can have the ability to access the virtual electrodes signal v.

In one embodiment, referring again to FIGS. 4 and 5, a simulator can include a motor intent unit, a motor pools unit, and an electrodes unit. The simulator can be written in a programming language (e.g., MATLAB, Python, C/C++, or JAVA) and can be executed using any suitable means known in the art, including but not limited to a GUI or a command line.

In a particular embodiment, simulation and user-specified parameters and functions are defined using one or more computer-accessible documents (e.g., several Microsoft Excel and/or text documents). In a further embodiment, the simulator can be web-based.

Motor intent is the vector u(t) (Equation 1) modeled as a set of independent functions over a time interval [0,T] specified by the user prior to the start of the simulation. A user can have the option to set each component of the vector u(t) as desired. For example, a user can set a motor intent to a pulse of a particular width, a ramp of a particular rise, duration and fall times, and/or a sinusoid with a specific frequency. Alternatively, a user can use dynamic models, for example an arm model, to generate motor intent signals for a task such as reaching. In many embodiments, the software will normalize the vector u(t) to be between (0, 1).

Part of the motor intent unit is the matrix G that maps motor intents to motor neurons activation states. Its structure and the values of its elements must be specified by the user (e.g., using a Microsoft Excel or text file) prior to the start of simulation. From the specification of the G map, the simulator software can determine the number of motor pools and the number of motor neurons per pool. Number of motor pools equals the dimension of the vector u (t). The default G is 10×1 matrix of ones—10 neurons in one motor pool.

The motor pools unit transforms motor intent signals to firings of motor neurons (Equations 2-9). The inputs to this unit are activation states of motor neurons, x(t). The outputs, y(t), are firing patterns carried on motor axons to target muscles. FIG. 4 depicts the processing steps that are carried on in this unit. An input/output response curve, a firing model (e.g. Poisson, Gaussian), and a spike template for each motor neuron can be specified by the user prior to the start of the simulation. Referring to FIGS. 3 and 4C, spike templates can be generated by a subunit of the simulator.

The electrodes recording unit is responsible for producing realistic neural firing for the recording electrodes. In one embodiment, the electrodes recording unit includes two main parts: motor axons to electrodes mapping matrix; and a noise model. The motor axons to electrode mapping matrix, H, depends on the electrodes placement and design. The user can specify this matrix in two different ways. The first method is a direct specification of the matrix. The other method is based on equations 11-13, where the map H is divided into block matrices for the LIFEs recording model.

The noise model used is a power-law noise, but the user can also specify band-limited Gaussian white noise. The user is able to specify a SNR ratio thus indirectly setting the noise intensity. Also, the user can set the noise bandwidth for band-limited noise or the exponent β for power-law noise. Each electrode will have its own noise input, and the SNR ratio can be calculated in the following manner:

$$SNR = \frac{Q_{99.9} - Q_{0.1}}{3\sigma_{noise}}, \quad (14)$$

where $Q_{99.9}$ and $Q_{0.1}$ are the 99.9% percentile and 0.1% percentile of the pure neural signal recorded by the electrode. $\sigma_{noise}$ is the standard deviation of the noise. The specified SNR ratio is used by the simulator to calculate the standard deviation of the noise model.

In one embodiment, a simulator requires that a user specify one or more of the following simulation parameters: input/output response curves for each motor neuron, including threshold motor intent and initial firing frequency and saturation motor intent and firing frequency (recruitment characteristics can be indirectly specified by the threshold motor intent and saturation point; spike template for each motor neuron, including spike shape, duration, and amplitude; the firing model (e.g., Poisson, Gaussian); motor intent to motor neuron mapping matrix, G; motor neuron to electrode mapping matrix, H; and noise model including SNR ratio and/or bandwidth. In a particular embodiment, the user must specify all of the preceding simulation parameters.

Though the mapping matrices G and H in the simulator can sometimes be assumed to be constant linear matrices, the connectivity between upper motor neurons and spinal motor neurons is not static and can change as a result of training or trauma (e.g., amputation, lesions, stroke). Also, groups of motor neurons within a motor pool could fire intermittently over time for a given level of motor intent. Thus, G varies over time and could possibly be a nonlinear function of motor intent. The H map, which maps motor axons to electrodes, depends on electrode placement, design, drift, and encapsulation. Therefore, the H map also changes over time. In many embodiments, it is assumed that this mapping is linear because, in an isotropic medium, electric fields sum linearly on electrodes. In certain embodiments, medium anisotropy, drift, and/or aging of the electrode-tissue interface can be accounted for. In a further embodiment, effects such as shielding of an electrode (e.g., by sensory axons from motor axons), encapsulation and/or electrode-tissue interface chemistry can be accounted for.

Figure 10:
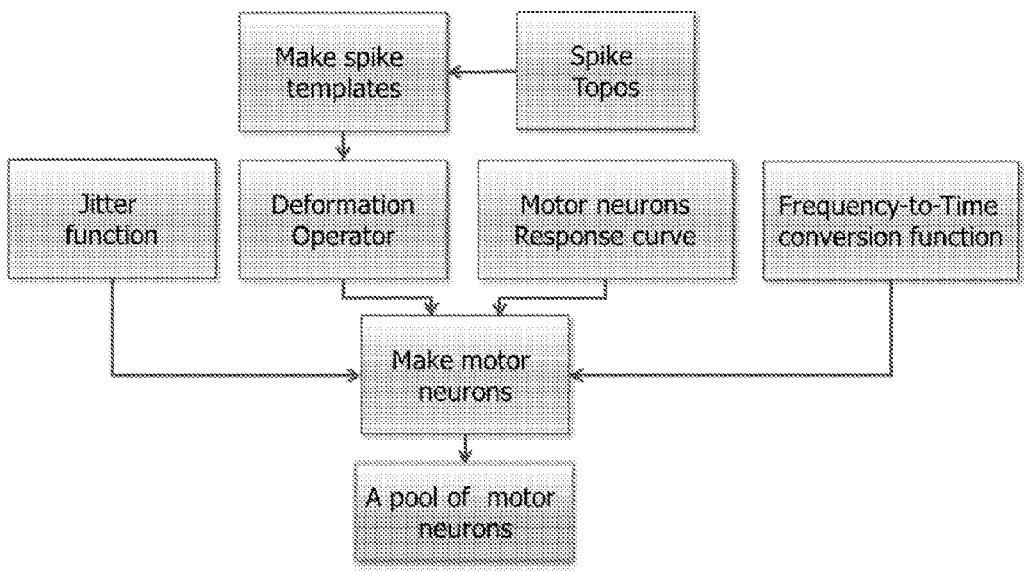
FIG. 10 shows a diagram of a simulator according to an embodiment of the subject invention.
Figure 11:
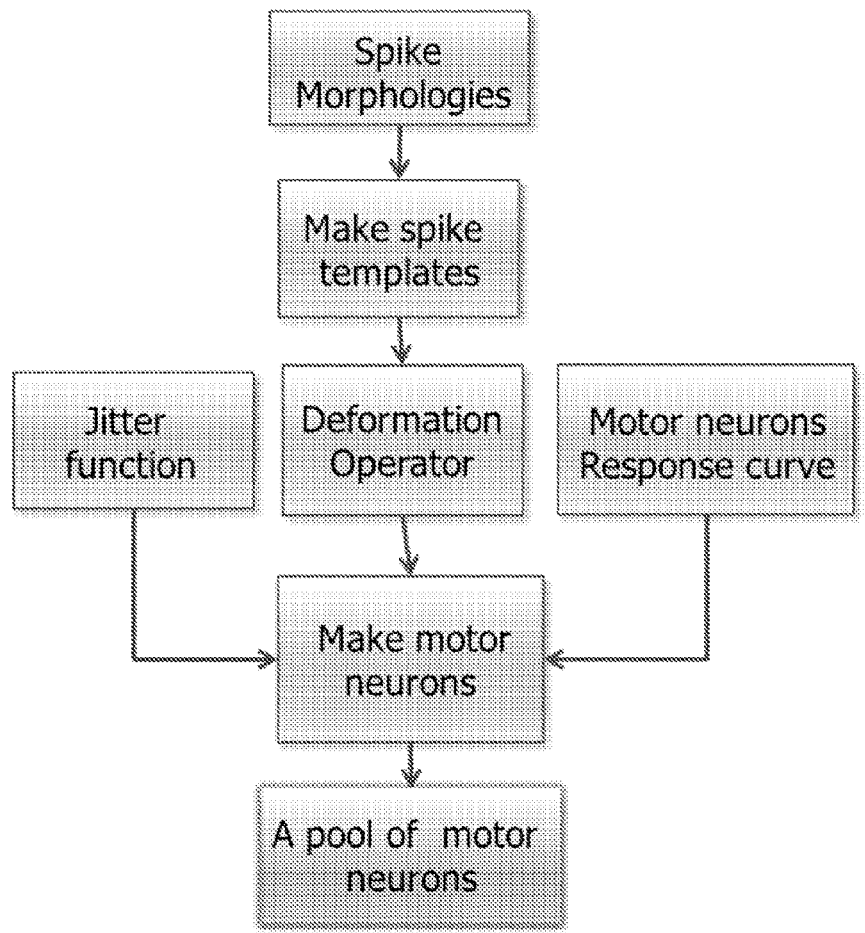
FIG. 11 shows a diagram of a simulator according to an embodiment of the subject invention.

FIGS. 10 and 11 show diagrams of a simulator according to an embodiment of the subject invention. Referring to FIGS. 10 and 11, the diagram shows the subunit responsible for creating pools of motor neurons. Generating spike templates from different spike topologies (morphologies} gives spike templates that can be used to construct trains of action potentials. The motor neurons response curve can determine neuron firing characteristics (e.g., fast, slow, intermediate), and recruitment characteristics, and the jitter function can be, e.g., uniform, Poisson, Gaussian. The frequency to time conversion function tells how the motor neuron converts frequency of indented firing to spikes timing (e.g., $F=1/T$ or $F=1/T^{1/2}$). This could be lumped with the motor neurons response curve.

Figure 12:
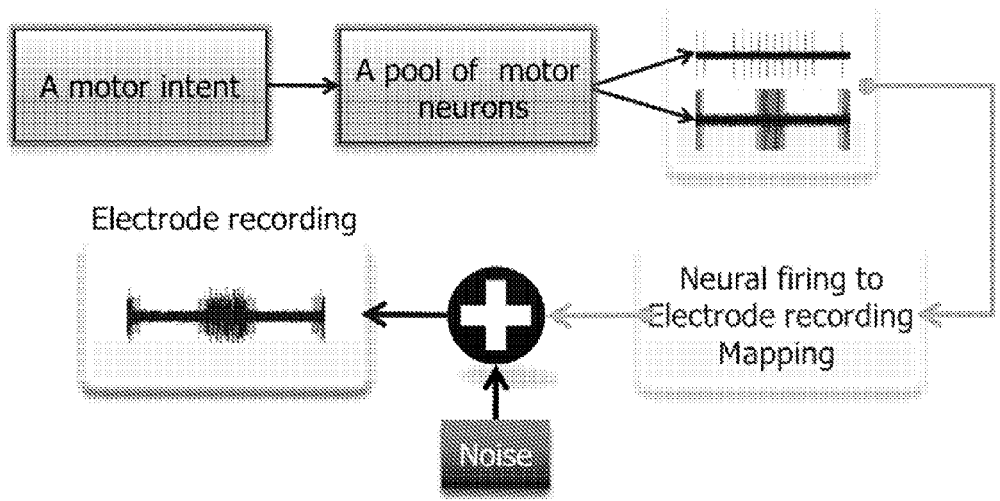
FIG. 12 shows a diagram of a simulator according to an embodiment of the subject invention.

FIG. 12 shows a diagram of a simulator according to an embodiment of the subject invention. Referring to FIG. 12, motor intent is transformed by a pool of motor neurons to spikes. Spikes from multiple motor axons can be recorded by LIFEs, and the LIFE recruitment matrix can specify which motor axons are recorded from simultaneously.

Figure 13:
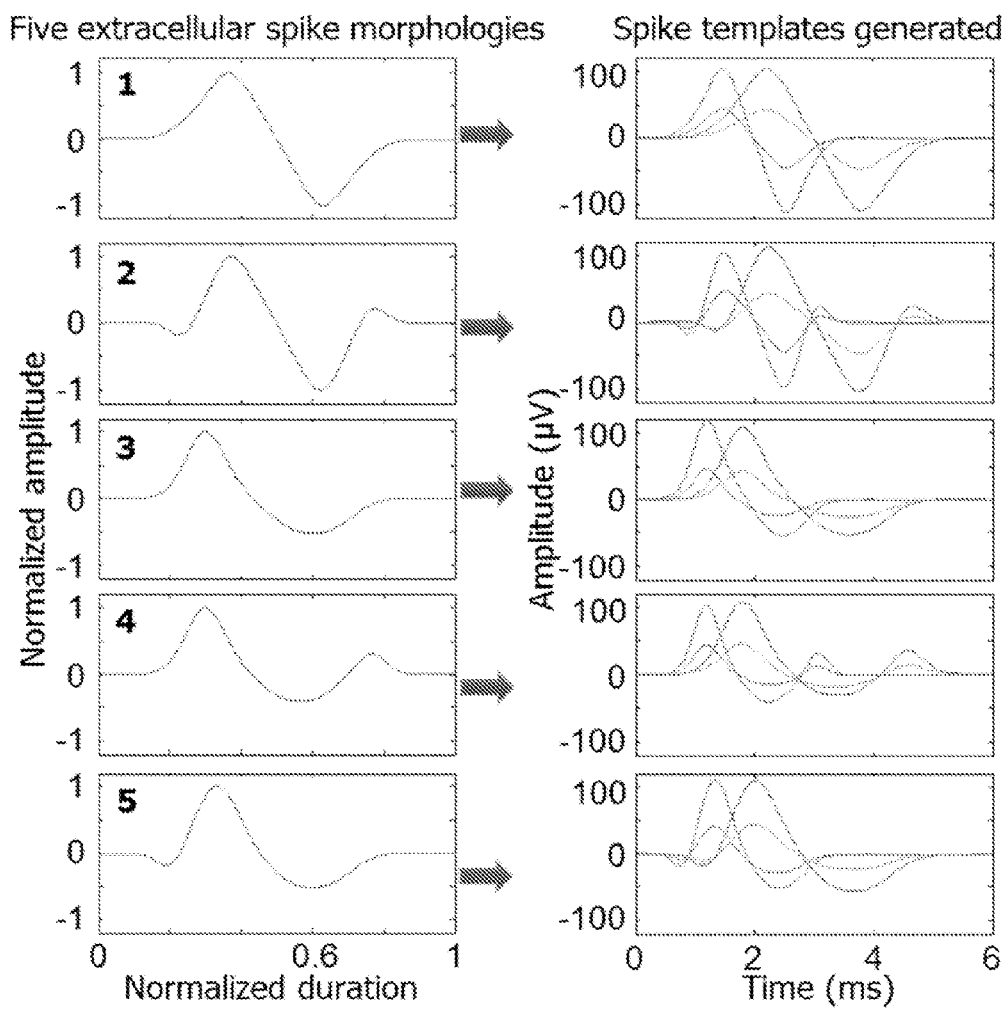
FIG. 13 shows plots of simulated spikes.

FIG. 13 shows plots of simulated spikes. Referring to FIG. 13, the spikes have variable shape, amplitude, and duration, and five extracellular spike topos are used.

Figure 14:
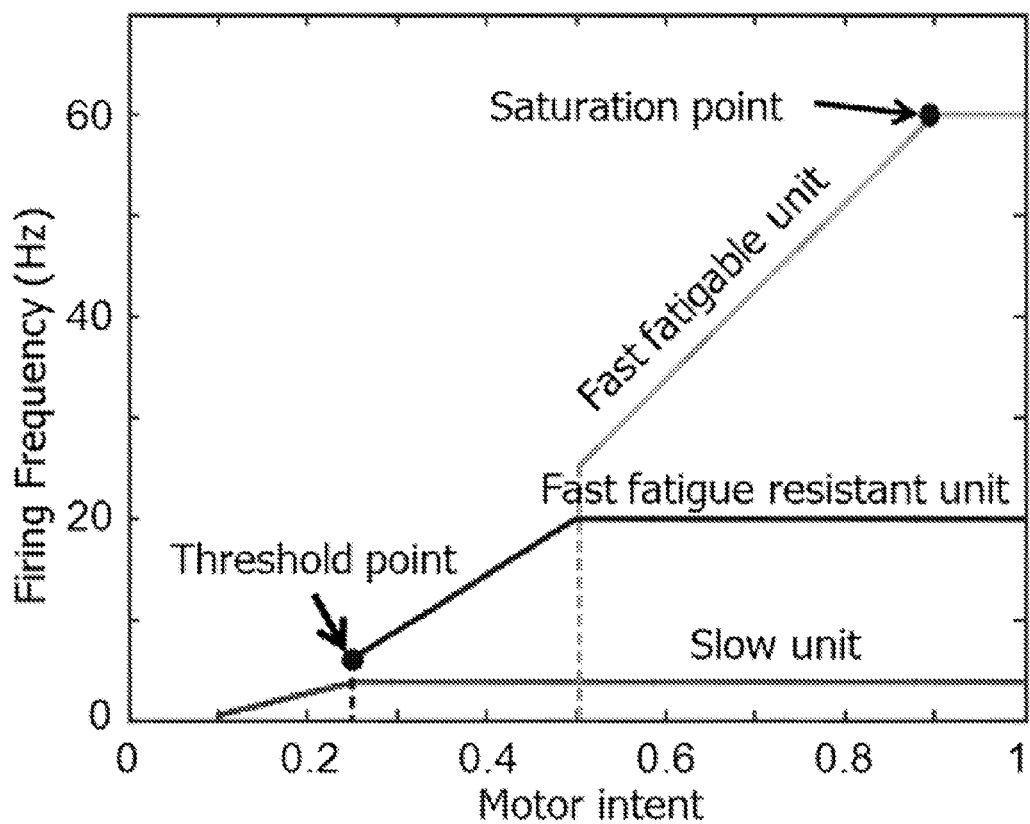
FIG. 14 shows a plot of firing frequency as a function of motor intent.

FIG. 14 shows a plot of firing frequency as a function of motor intent. Referring to FIG. 5, motor intent is between 0 and 1. Zero is null motor effort while 1 is maximum motor effort. Saturation is the maximum firing of a motor neuron, and threshold is the level of motor intent above which motor neurons will begin to fire. The variability of thresholds between motor neurons is determined by a population recruitment function.

Figure 15:
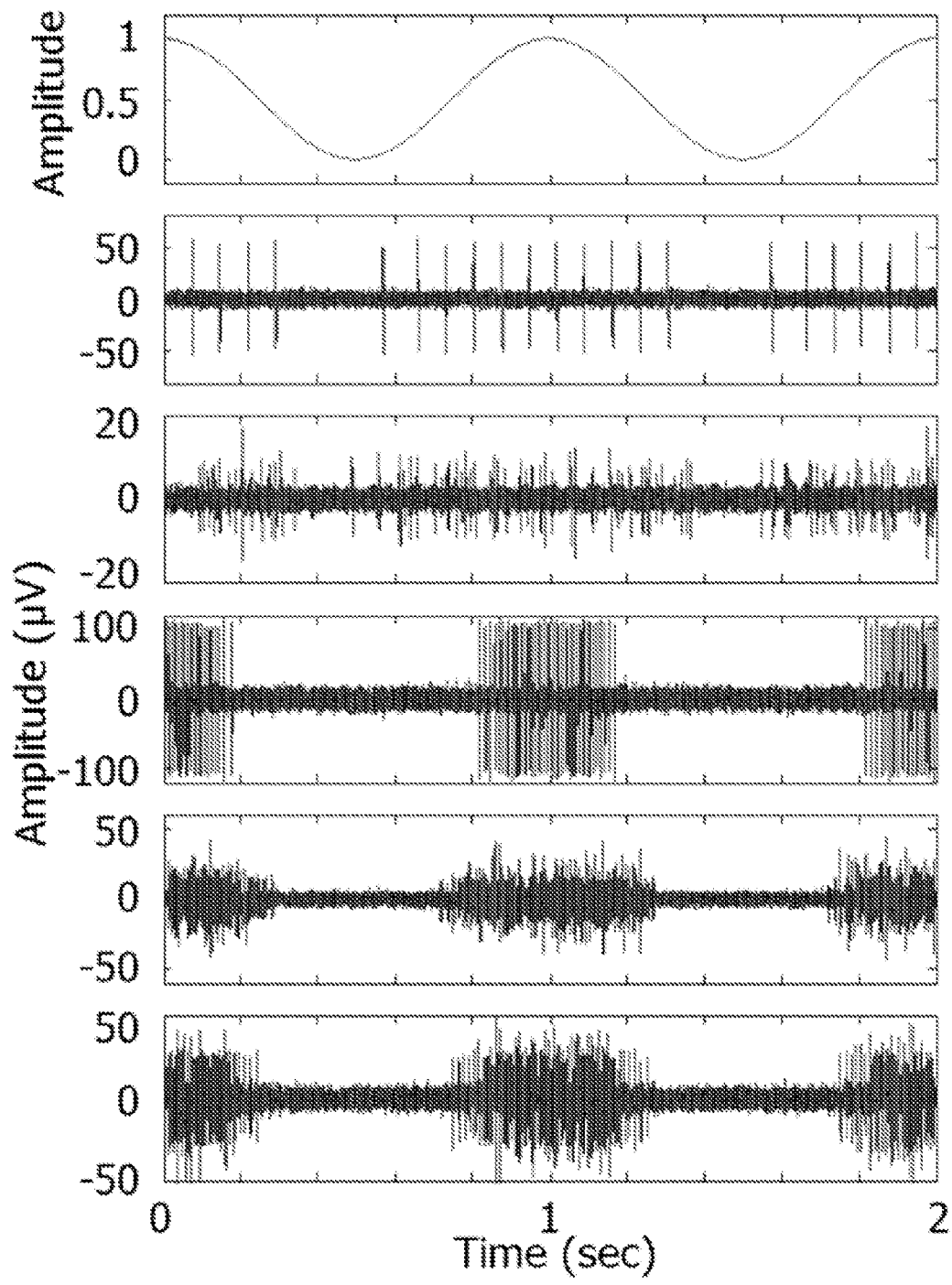
FIG. 15 shows plots of neural recordings.

FIG. 15 shows plots of neural recordings. Referring to FIG. 15, LIFEs neural recordings from fast and slow motor units are shown. To estimate motor intent with sufficient accuracy, a decoding algorithm must be able to handle recordings from different subsets of different motor fibers. Different motor fibers contribute different firing patterns and spike shapes to LIFE electrodes recording. Slow motor fibers have sparse firing, longer spike duration, and smaller amplitudes while fast fibers have larger amplitudes, shorter spikes, and denser firing patterns. LIFE electrodes, depending where they are placed in a nerve fascicle, could pick activity from slow, fast, or a mix of motor fibers.

Figure 16:
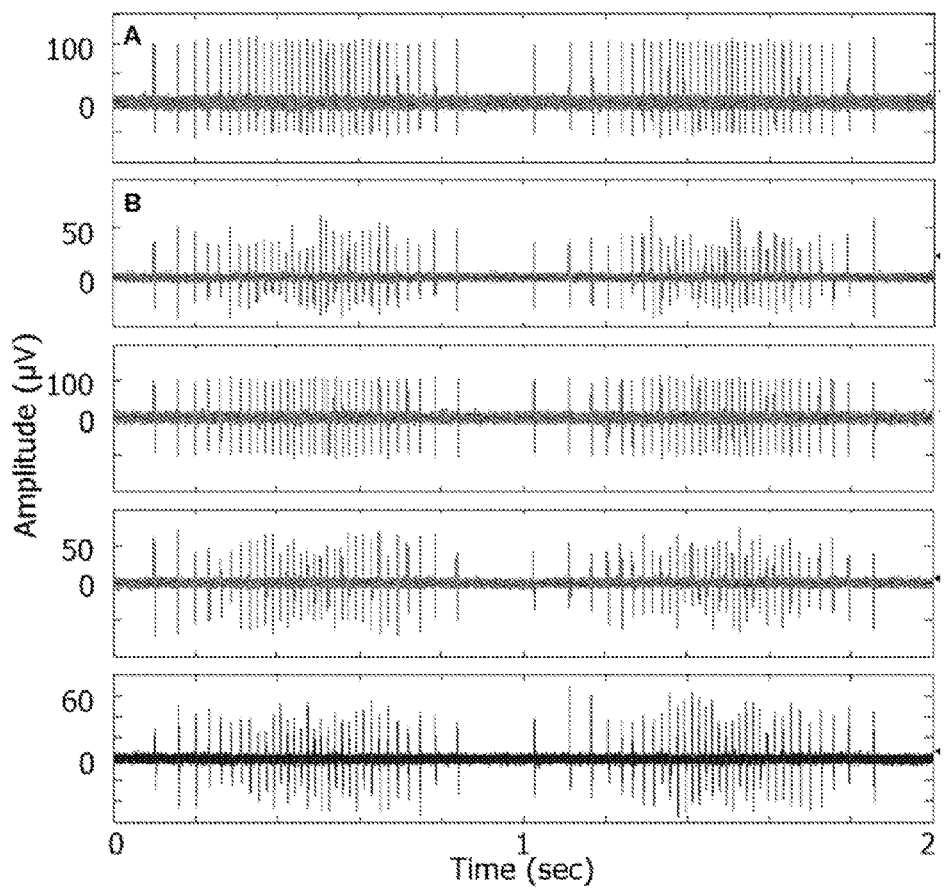
FIG. 16 shows plots of neural recordings.

FIG. 16 shows plots of neural recordings. Referring to FIG. 16, LIFE neural recordings from motor neurons with different extracellular spike shapes are shown. Different spike shapes alter the pattern of neural recordings by LIFE electrodes in various ways, thereby affecting the accuracy of decoding algorithms. Asymmetric spikes have a large and sharp positive peak but shallow and broad negative peak. A decoding algorithm that depends on a simple thresholding of positive peaks will perform differently than one that depends on thresholding of negative peaks. What the spike shapes look like in real neural recording is not known a priori. It is possible that spikes of different shape asymmetry can add on a single electrode recording. A decoding algorithm must be robust to changes in spike shapes.

Figure 17:
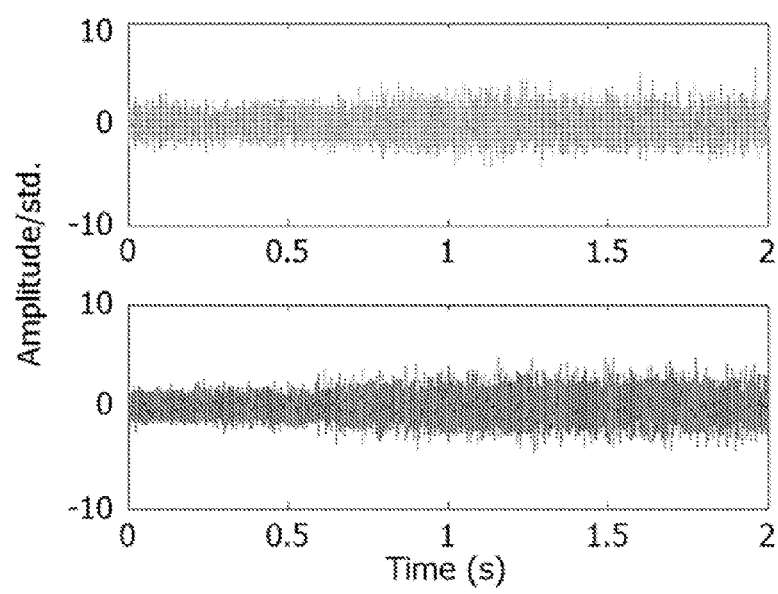
FIG. 17 shows a comparison of simulator data with LIFE-recorded data.

FIG. 17 shows a comparison of simulator data with LIFE-recorded data. Referring to FIG. 17, simulated and experimental data were generated using the ramp and hold motor intent. Amplitudes of both data were scaled using the standard deviation of the Quiescent phase (i.e., a null motor intent), and a moving-window t-test (200 ms) between simulated and experimental data shows that they are not significantly different from each other (h=0).

Figure 18:
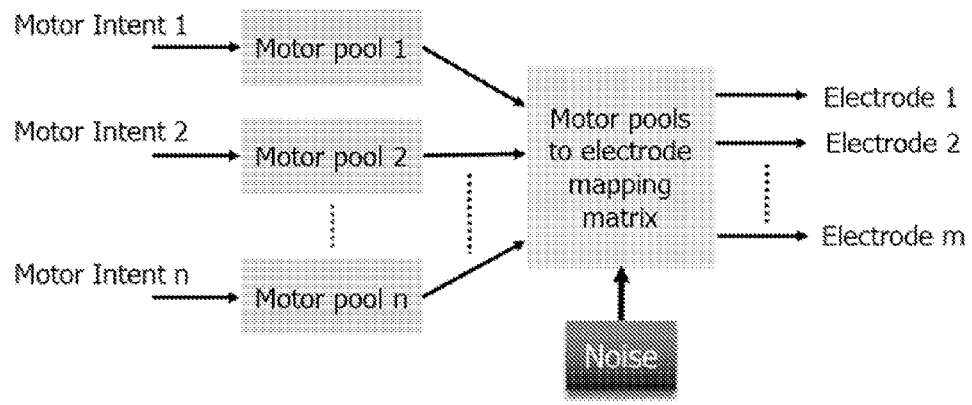
FIG. 18 shows a diagram of a motor control system according to an embodiment of the subject invention.

FIG. 18 shows a diagram of a motor control system according to an embodiment of the subject invention. Referring to FIG. 18, global architecture of a LIFE simulator is shown. The LIFEs simulator can be configured to mimic the functional characteristics of motor control and to record from LIFE electrodes.

Figure 19:
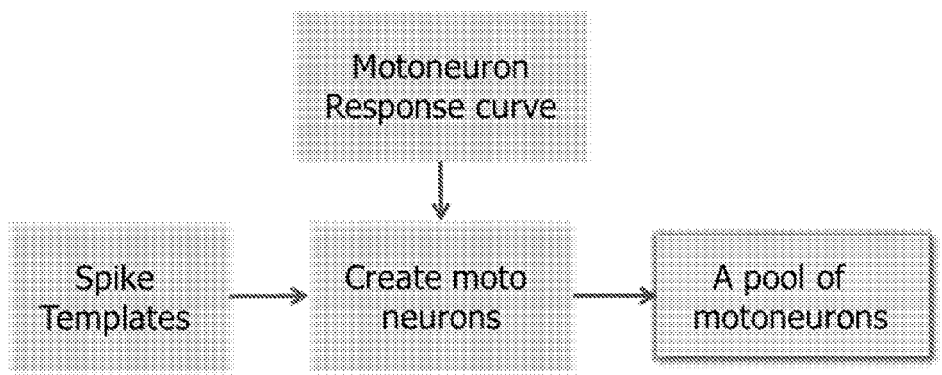
FIG. 19 shows a diagram of a simulator according to an embodiment of the subject invention.

FIG. 19 shows a diagram of a simulator according to an embodiment of the subject invention. Referring to FIG. 19, a pool of motor neurons with specific properties can be designed. Components of the LIFEs simulator are shown, specifically subunits responsible for creating pools of motor neurons.

Figure 20:
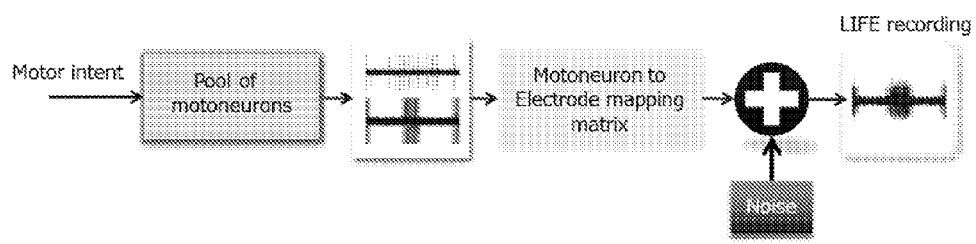
FIG. 20 shows a diagram of a simulator according to an embodiment of the subject invention.

FIG. 20 shows a diagram of a simulator according to an embodiment of the subject invention. Referring to FIG. 20, motor intent can be transformed to spikes and then to LIFEs recordings. Motor intent can be transformed by a pool of motoneurons to spikes. Spikes from multiple motor axons can be recorded by LIFEs, and the mapping matrix can determine the mapping between motoneurons and the electrode recording.

Figure 21:
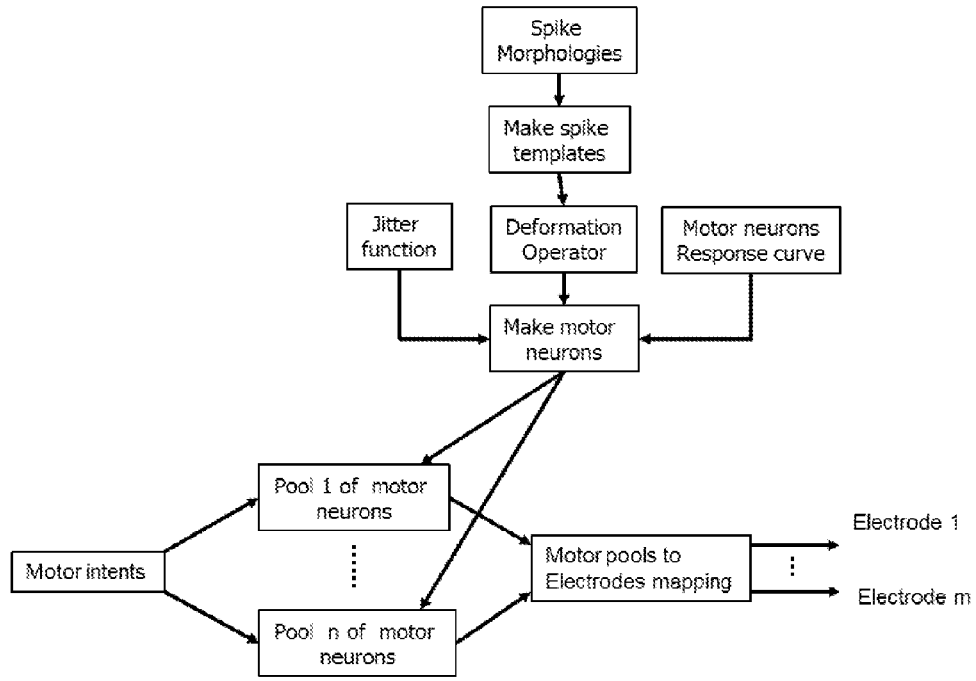
FIG. 21 shows a diagram of a simulator according to an embodiment of the subject invention.

FIG. 21 shows a diagram of a simulator according to an embodiment of the subject invention. Referring to FIG. 21, the architecture of a simulator is shown.

Figure 22:
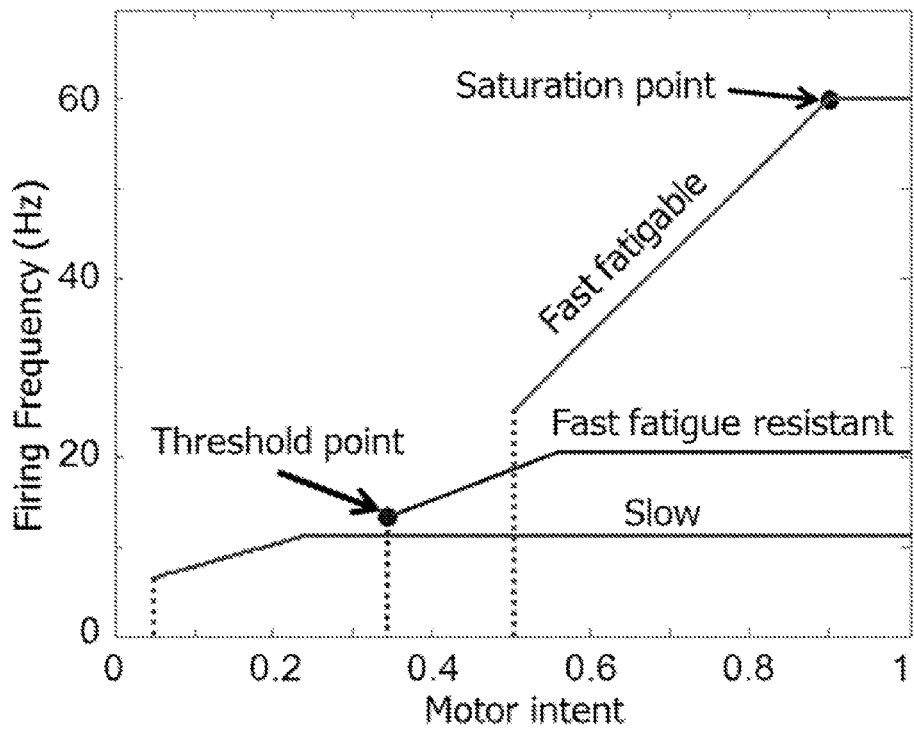
FIG. 22 shows a plot of firing frequency as a function of motor intent.

FIG. 22 shows a plot of firing frequency as a function of motor intent. Referring to FIG. 22, examples of motoneuron response curves are shown. Motor intent is between 0 and 1, where zero is null motor effort and one is maximum motor effort. Threshold is the level of motor intent above which motoneuron will begin to fire, and saturation is the maximum firing of a motoneuron.

Figure 23:
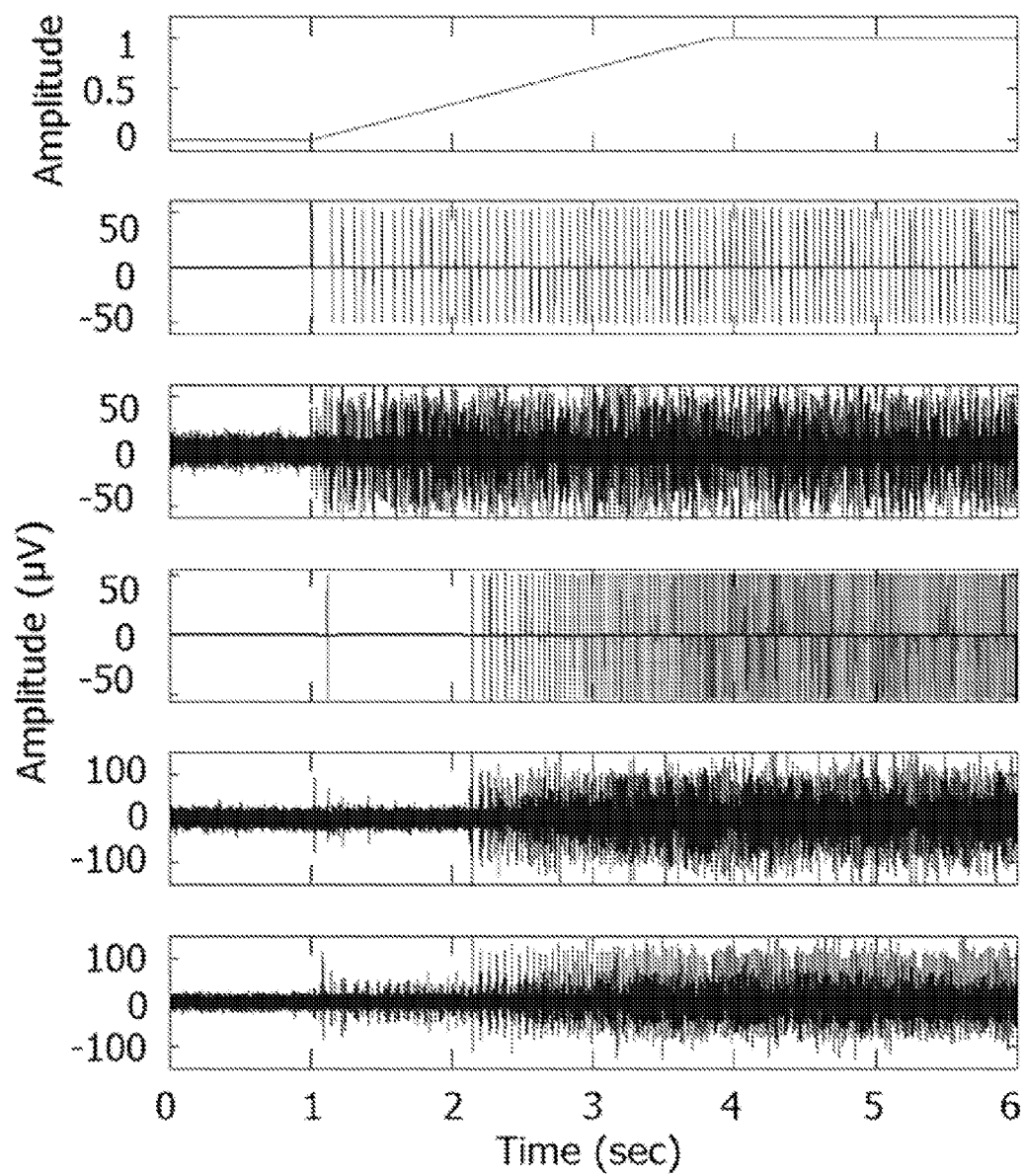
FIG. 23 shows plots of neural recordings.

FIG. 23 shows plots of neural recordings. Referring to FIG. 23, LIFEs neural recording from fast and slow motor units for ramp up motor intent are shown. From the top and going down, the recording shows: motor intent; firing of a slow motor fiber; a LIFE recording of slow motor fibers; firing of a fast motor fiber; a LIFE recording of fast motor fibers; and a LIFE recording of fast and slow motor fibers.

Figure 24:
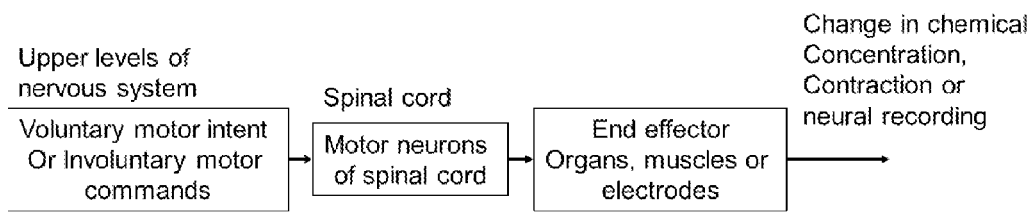
FIG. 24 shows a diagram of a simulator according to an embodiment of the subject invention.

FIG. 24 shows a diagram of a simulator according to an embodiment of the subject invention. Referring to FIG. 24, one or more organs and/or muscles can be used as an end effector.

Figure 25:
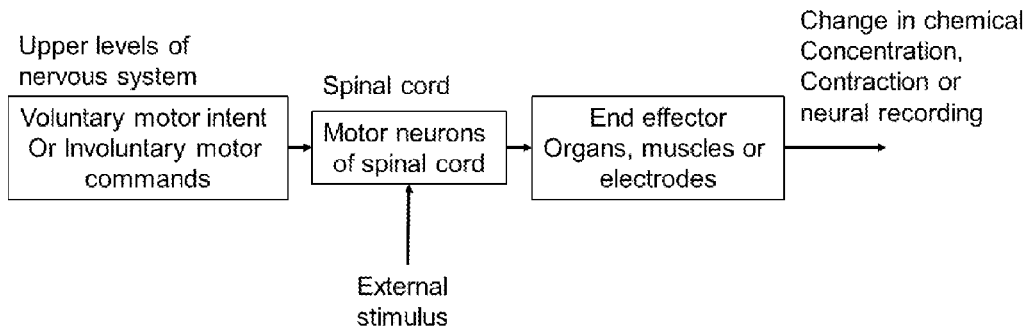
FIG. 25 shows a diagram of a simulator according to an embodiment of the subject invention.

FIG. 25 shows a diagram of a simulator according to an embodiment of the subject invention. Referring to FIG. 25, at least one external stimulus can be applied to the spinal cord.

Figure 26:
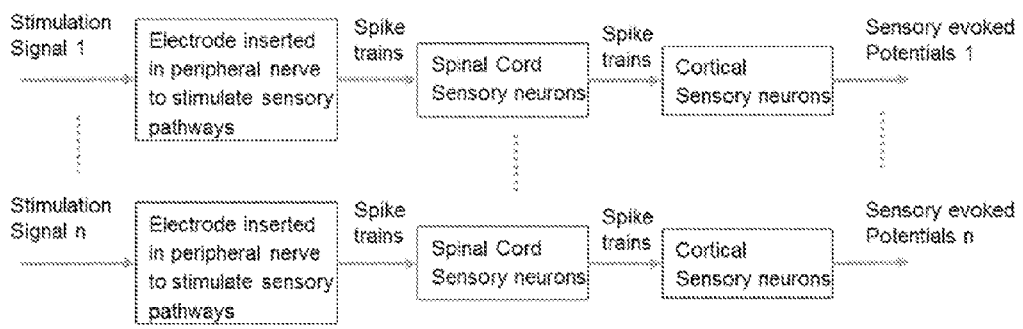
FIG. 26 shows a diagram of a simulator according to an embodiment of the subject invention.

FIG. 26 shows a diagram of a simulator according to an embodiment of the subject invention. Referring to FIG. 26, sensory evoked potentials can be stimulated as a result of stimulation by peripheral neural electrodes.

Figure 27:
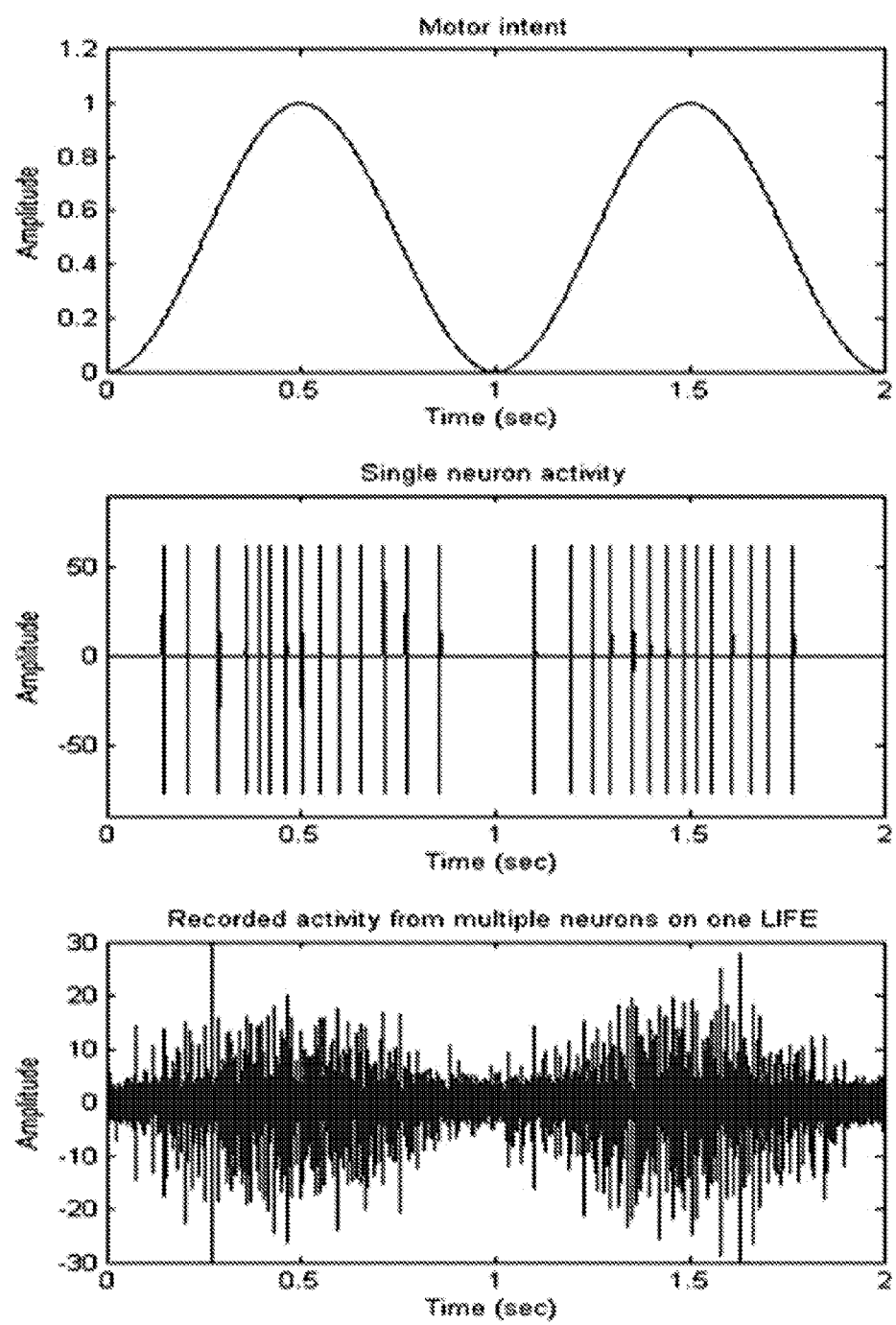
FIG. 27 shows recordings from a simulator according to an embodiment of the subject invention.

FIG. 27 shows recordings from a simulator according to an embodiment of the subject invention. Referring to FIG. 27, the signals to be recorded from LIFE electrodes can be simulated. A presumed motor intent signal can be translated from the user to generate a simulated recording from a LIFE electrode. Motor intent (top plot) drives a pool of simulated motor neurons with various spike shapes, recruitment characteristics, and firing rate properties (output of one motoneuron shown in center plot). Each LIFE can record a weighted sum of a subset of simulated motoneuron activity patterns (bottom plot). Several types of noise can be included in the signal path.

Figure 28:
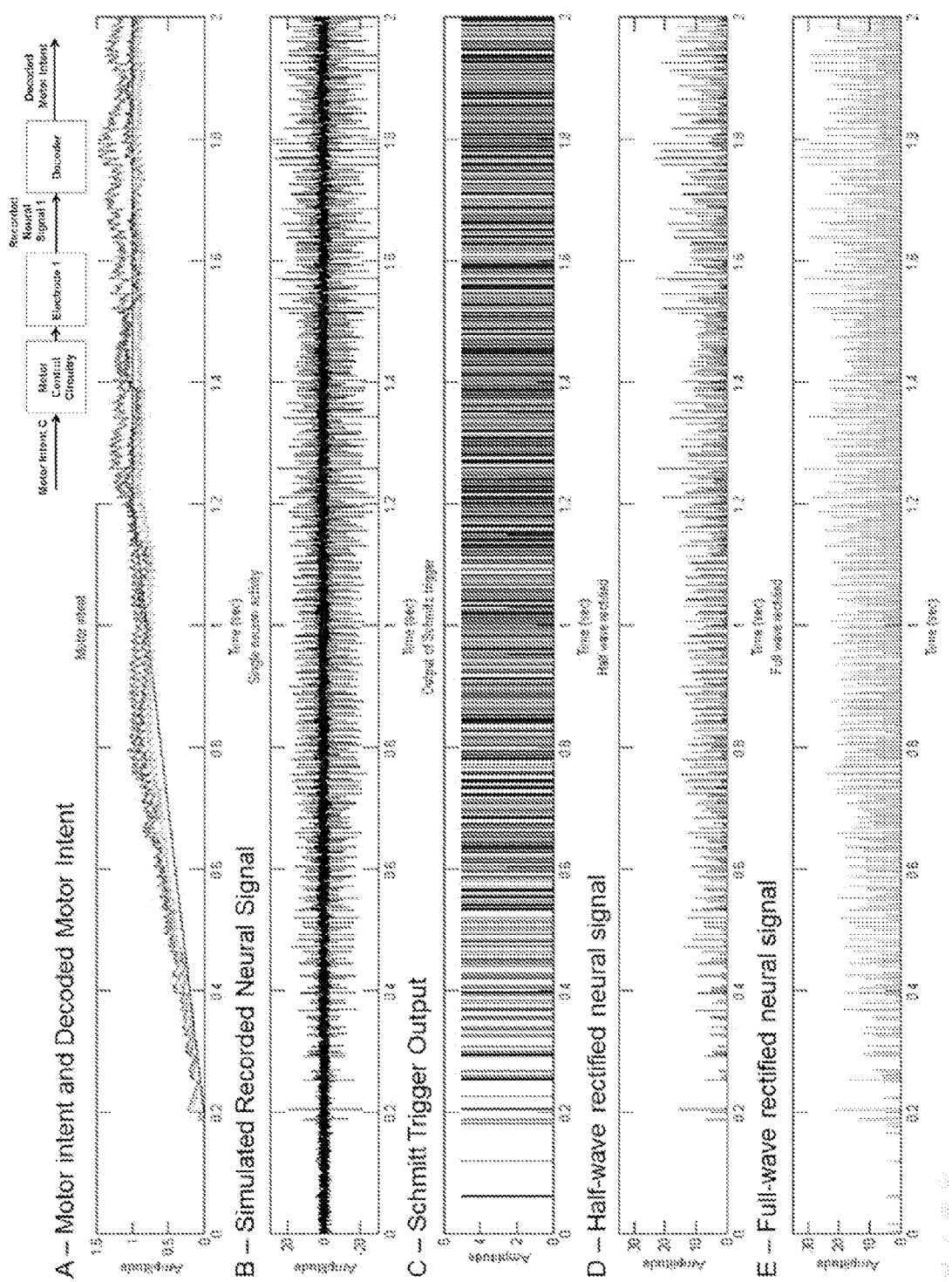
FIG. 28 shows a diagram of a simulator according to an embodiment of the subject invention and recordings from a simulator according to an embodiment of the subject invention.

FIG. 28 shows a diagram of a simulator according to an embodiment of the subject invention and recordings from a simulator according to an embodiment of the subject invention. Referring to FIG. 28, from the top and going down, shown is a diagram of a system according to an embodiment of the subject invention, a recording of motor intent and decoded motor line, a simulated recorded neural signal, a Schmitt trigger output (exponential moving average of 100 milliseconds), a half-wave rectified neural signal(exponential moving average of 100 milliseconds), and a full-wave rectified neural signal(exponential moving average of 100 milliseconds).

Figure 29:
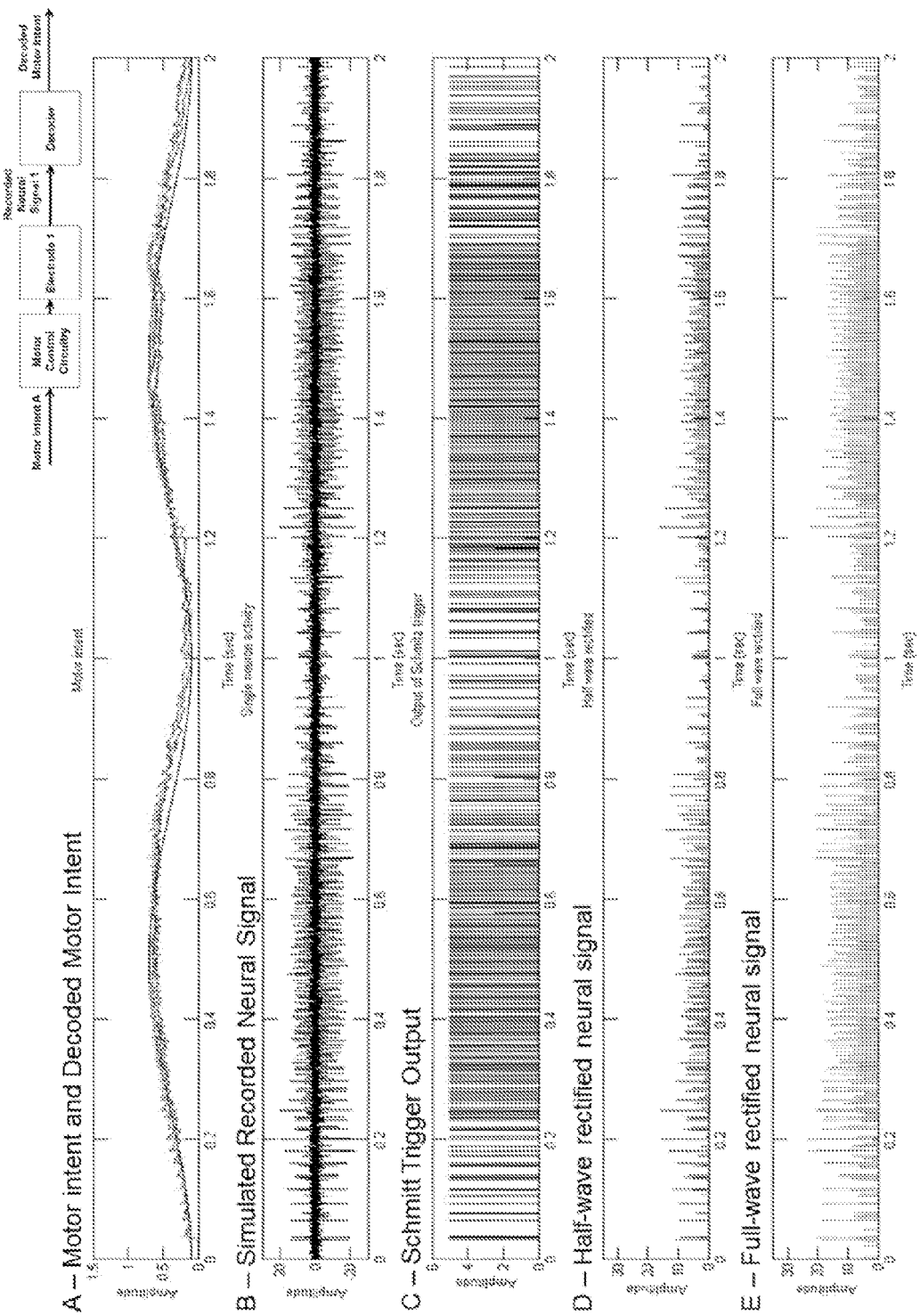
FIG. 29 shows a diagram of a simulator according to an embodiment of the subject invention and recordings from a simulator according to an embodiment of the subject invention.

FIG. 29 shows a diagram of a simulator according to an embodiment of the subject invention and recordings from a simulator according to an embodiment of the subject invention. Referring to FIG. 29, from the top and going down, shown is a diagram of a system according to an embodiment of the subject invention, a recording of motor intent and decoded motor line, a simulated recorded neural signal, a Schmitt trigger output (exponential moving average of 100 milliseconds), a half-wave rectified neural signal(exponential moving average of 100 milliseconds), and a full-wave rectified neural signal(exponential moving average of 100 milliseconds).

Figure 30:
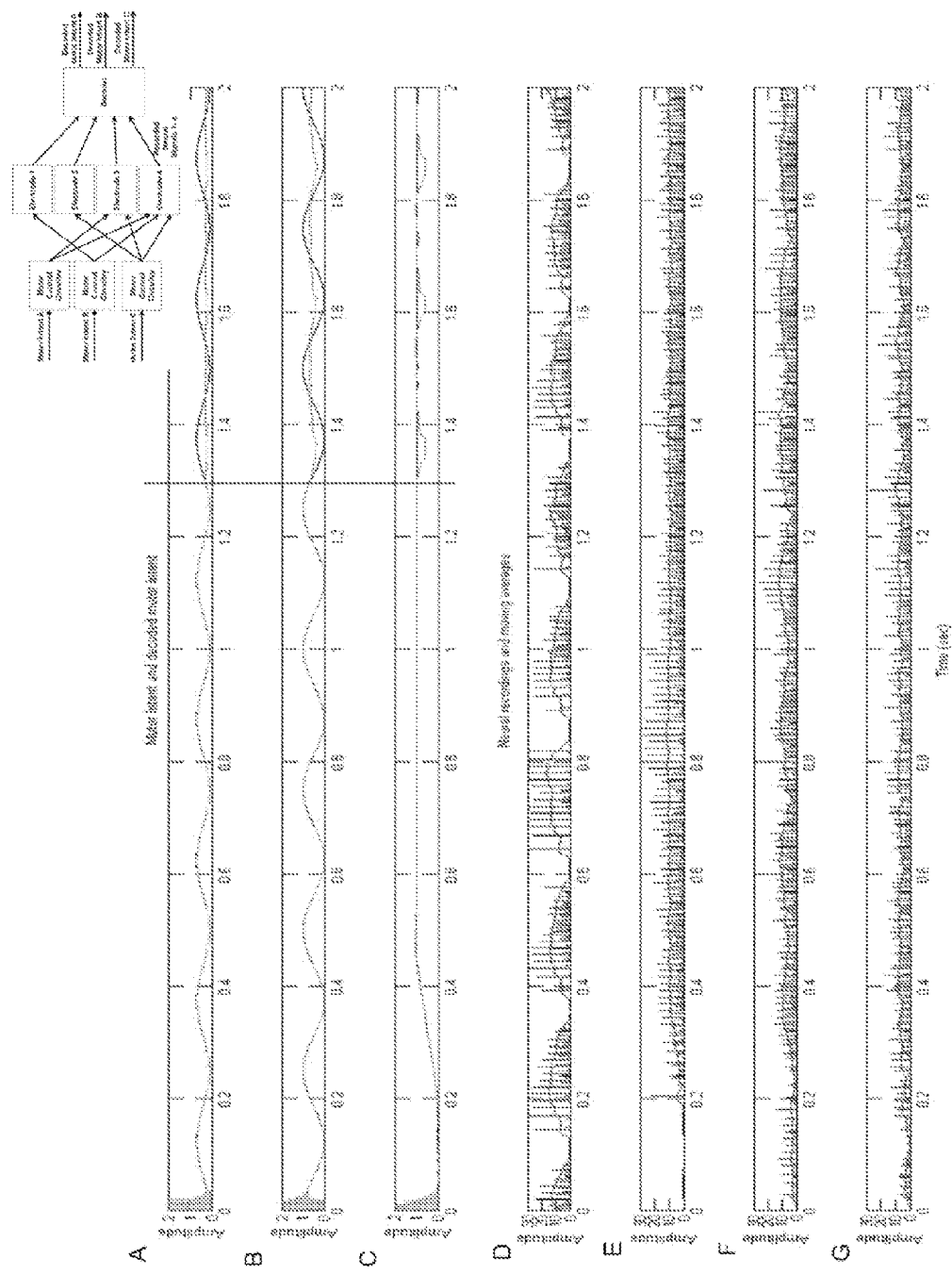
FIG. 30 shows a diagram of a simulator according to an embodiment of the subject invention and recordings from a simulator according to an embodiment of the subject invention.

FIG. 30 shows a diagram of a simulator according to an embodiment of the subject invention and recordings from a simulator according to an embodiment of the subject invention. Referring to FIG. 30, from the top and going down, shown is a diagram of a system according to an embodiment of the subject invention, a recording of a motor intent signal, another recording of a motor intent signal, yet another recording of a motor intent signal, a half-wave rectified recorded neural signal with moving averages for electrodes 1 and 2, another half-wave rectified recorded neural signal with moving averages for electrodes 1 and 2, a half-wave rectified recorded neural signal with moving averages for electrode 3, and a half-wave rectified recorded neural signal with moving averages for electrode 4.

Figure 31:
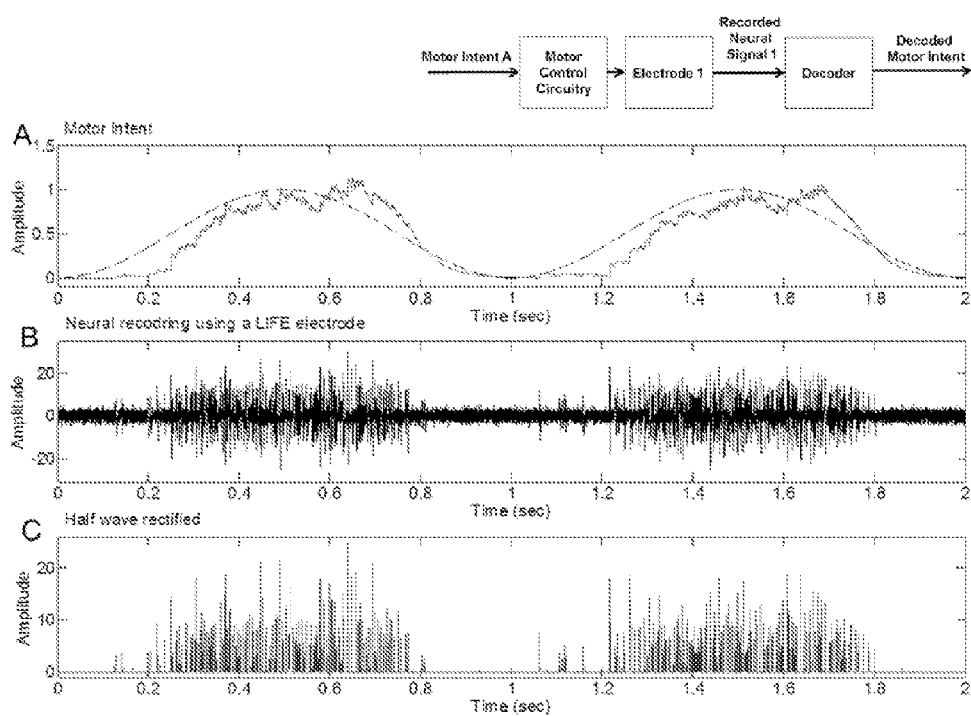
FIG. 31 shows a diagram of a simulator according to embodiment of the subject invention and recordings from a simulator according to an embodiment of the subject invention.

FIG. 31 shows a diagram of a simulator according to an embodiment of the subject invention and recordings from a simulator according to an embodiment of the subject invention. Referring to FIG. 31, the signals are simulations of a LIFE electrode.

Figure 32:
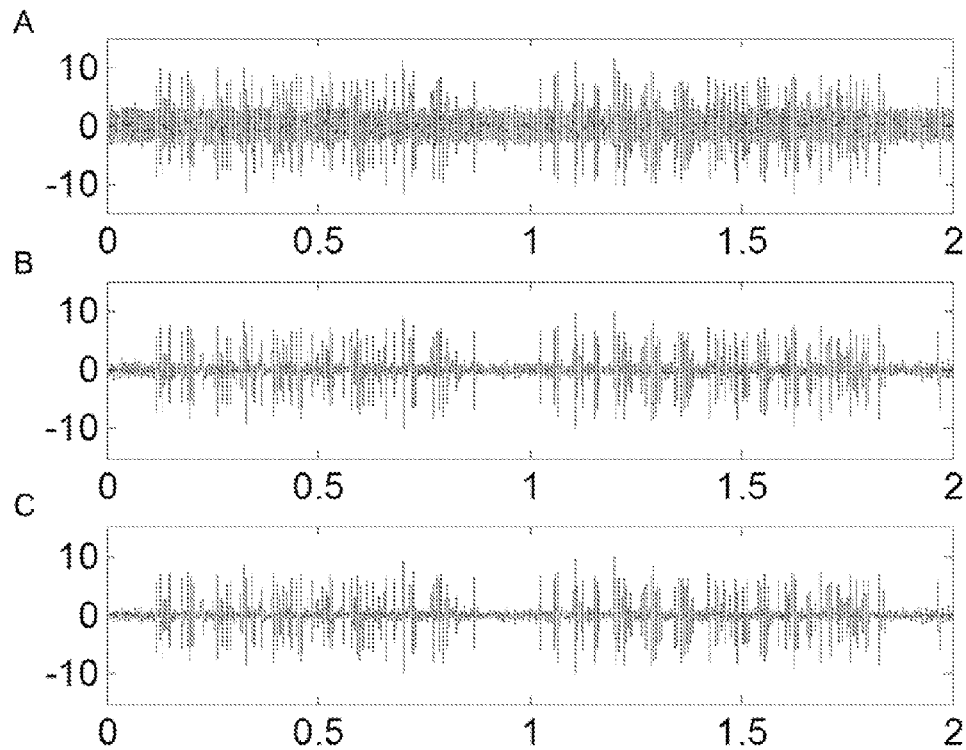
FIG. 32 shows signals conditioned by a Wavelet method.

FIG. 32 shows signals conditioned by a Wavelet method. Referring to FIG. 32, from the top and going down, shown are noisy simulated LIFE neural data, Wavelet de-noising using standard deviation of Quiescent phase of neural recording (i.e., subject is making no movement), and Wavelet de-noising using kurtosis of Quiescent phase.

Figure 33:
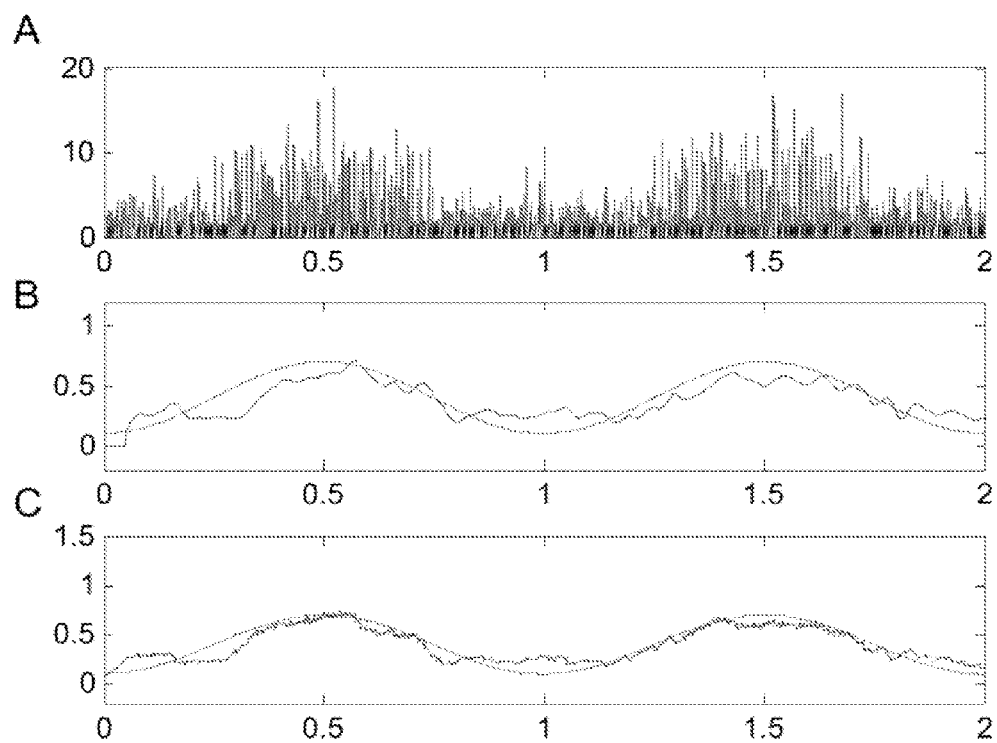
FIG. 33 shows neural signals.

FIG. 33 shows neural signals. Referring to FIG. 33, from the top and going down, shown are half-wave rectified simulated LIFE neural data, actual motor intent and Gaussian filtered motor intent, and actual motor intent and half-Gaussian filtered motor intent.

Figure 34:
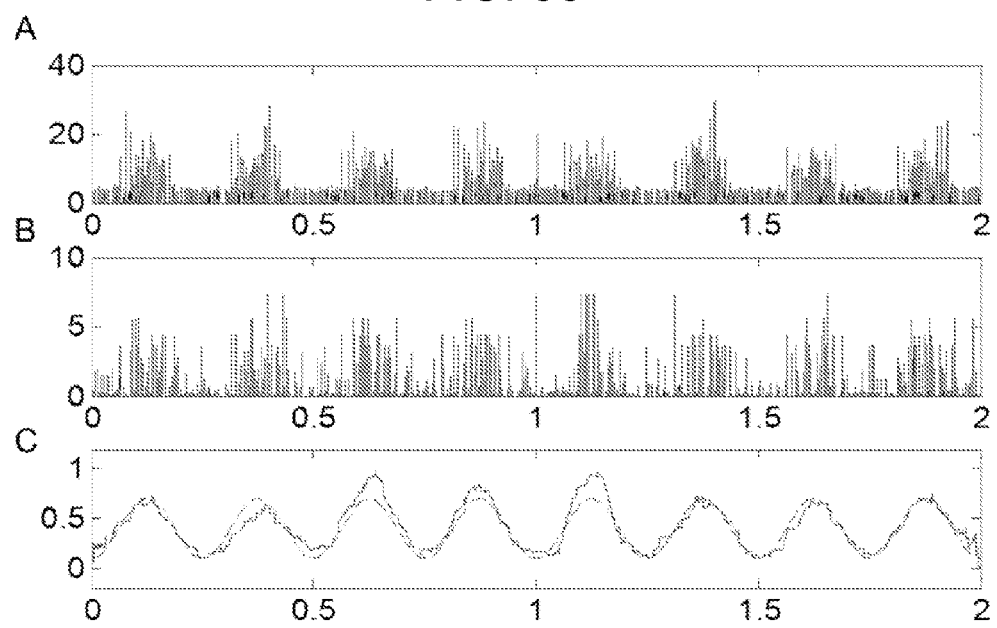
FIG. 34 shows neural signals.

FIG. 34 shows neural signals. Referring to FIG. 34, from the top and going down, shown are half-wave rectified simulated LIFE neural data, inverse of interspike intervals (i.e., frequency of firing), and actual motor intent and moving average of the frequency of firing motor intent.

Figure 35:
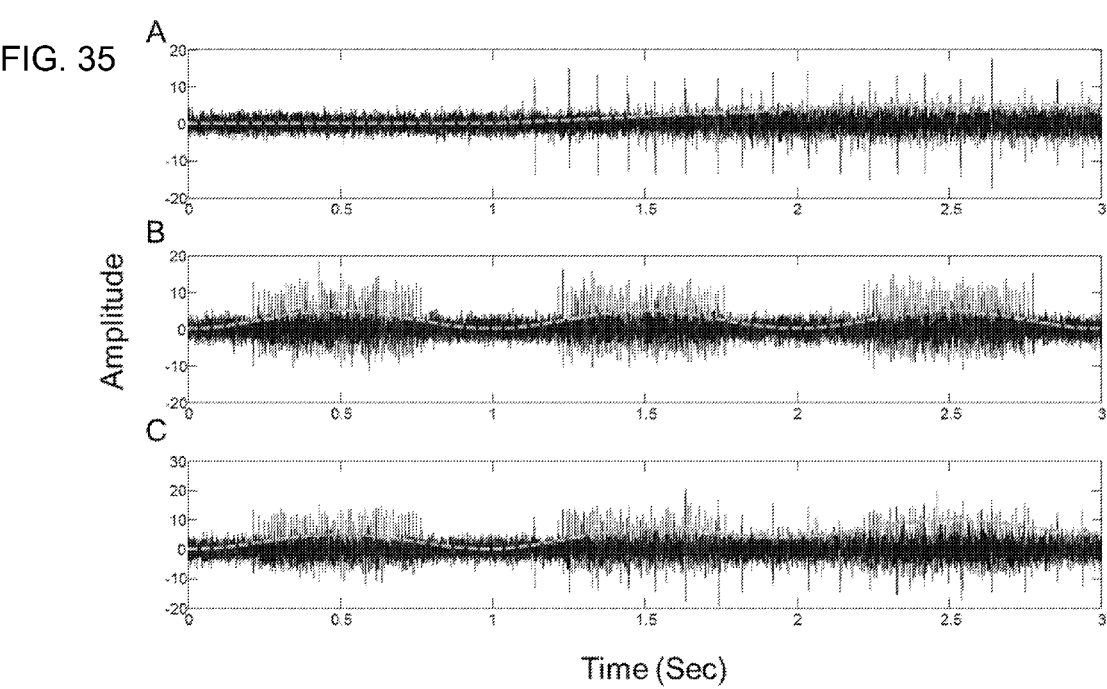
FIG. 35 shows neural signals.

FIG. 35 shows neural signals. Referring to FIG. 35, simulations of recording from three LIFEs, each receiving a different motor intent input signal, are shown. From the top and going down, the inputs are ramp and hold, rhythmic, and rhythmic+ramp and hold motor intent.

Figure 36:
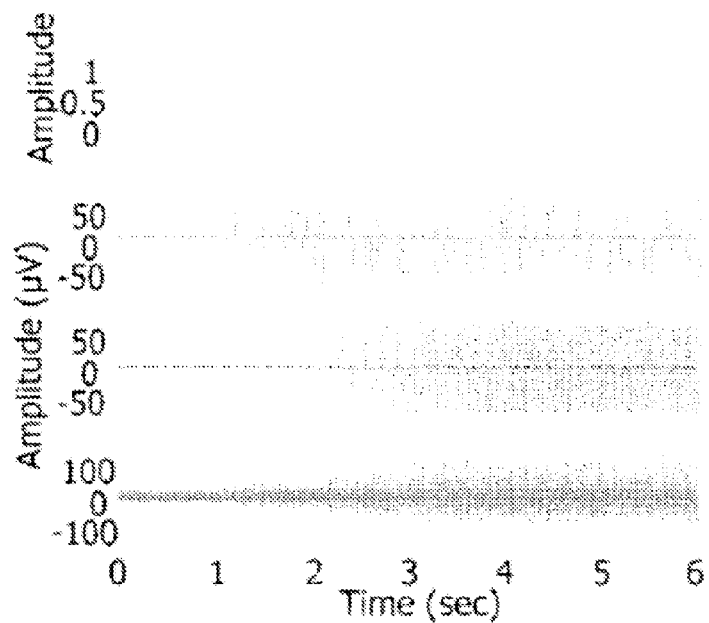
FIG. 36 shows neural signals

FIG. 36 shows neural signals. Referring to FIG. 36, from the top and going down, shown are motor intent, slow motor neuron firing, fast motor neuron firing, and LIFE recording of motor neuron activity.

Figure 37:
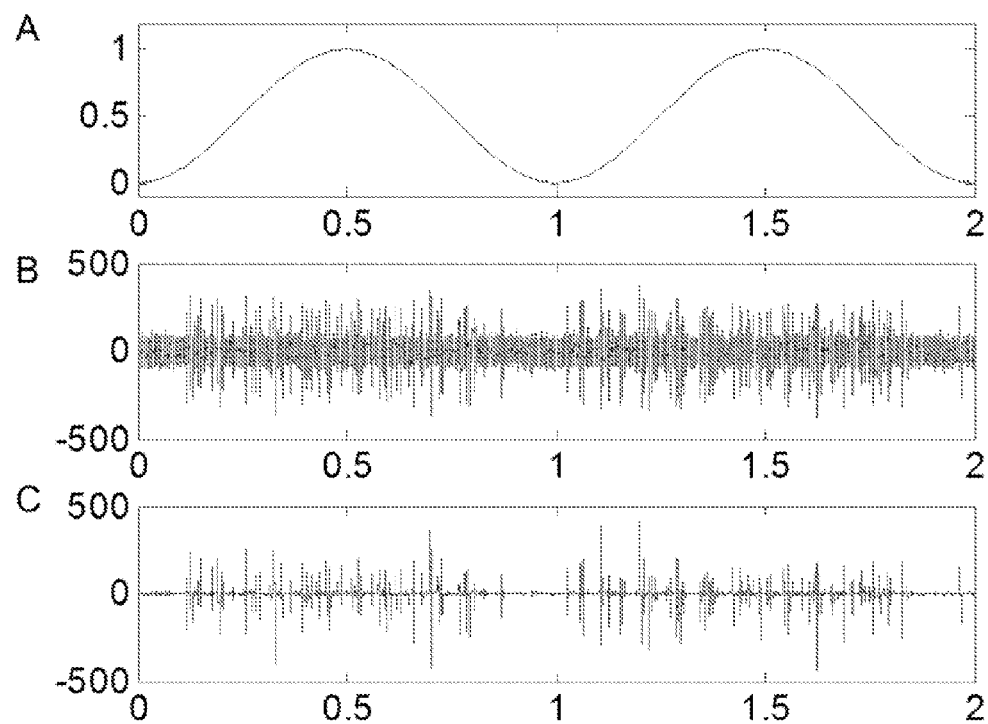
FIG. 37 shows neural signals.

FIG. 37 shows neural signals. Referring to FIG. 37, signal conditioning using nonlinear transformation method is shown. From the top and going down, shown are motor intent, noisy simulated LIFE neural data, and de-noised and enhanced data. The background noise is reduced and the spikes are amplified. This is easier to implement in hardware with inherent nonlinear methods.

In one embodiment, a method of simulating neural activity includes performing a simulation or mathematical model as described herein (e.g., running such a simulation or model on a computing device).

Systems and methods of the subject invention advantageously contribute to: the development of neural prostheses, including design of neural interfaces for stimulation of nerves for neuromodulation; the design of neural interfaces for recording nerve activity for control of prostheses; medical diagnostics of peripheral nerve disease; model systems to assess parameters for nerve stimulation for regional anesthesia; and educational training software and firmware for teaching neuroscience.

Systems and methods of the subject invention provide a computational platform for translating voluntary motor intent or involuntary motor output generated in the brain or spinal cord to neural recordings from peripheral nerves using different types of electrodes and interface technology. A simulator can be used for the translation of motor intent/output to peripheral nerve recordings. The simulator can be contained in software or firmware.

Systems and methods of the subject invention can simulate: neural recordings for a variety of peripheral neural interfaces such as point electrodes, longitudinal or transverse intrafascicular electrodes, CUFF electrodes, and multielectrode arrays that interface with peripheral nerves; electromyogram activity of muscles innervated by motor pools; the behavior of a variety of motor neurons (input-output response, such as threshold, saturation, and firing rates and spike characteristics including shape, duration, and amplitude); a variety of electrode tissue interface characteristics (e.g., encapsulation, electrode impedance, and electrode drift); and a variety of recording conditions such as level of ambient noise and recording systems characteristics.

Systems and methods of the subject invention can facilitate the development of neural decoding algorithms, produce data sets to test hypotheses about motor control and interaction of the nervous system with neural interfaces, and simulate abnormal peripheral nerve recordings reflecting different neurological disorders (e.g., motor neuron diseases). The resulting simulated signals can be analyzed and used to predict and classify possible causes of motor disorders. Hence, the diagnosis of neurological disorders can be aided. Also, motor intent (i.e., intention of a person to accomplish a motor task) can be converted to patterns of neural activity, and involuntary motor output can be converted to patterns of neural activity in peripheral nerves.

A simulator according to an embodiment of the subject invention can be used to evaluate the ability of neural activity to control an endeffector (e.g., a prosthetic limb). Further, nerve stimulation protocols can be designed for interventions, such as stimulation for regional anesthesia, partial paralysis, footdrop, gastric stimulation (gastroparesis), phrenic nerve stimulation (respiratory control), vagal nerve stimulation, and other peripheral nerves stimulation applications.

Systems and methods of the subject invention can facilitate the development of decoding algorithms which are essential for neural control of prostheses, as well as cut down on simulation time and be used as a diagnostic tool. Systems and methods can also be used for rapid testing of experimental paradigms and for testing hypotheses in cases when real data is not available, thereby saving time and money that would have been spent in conducting real experiments.

In many embodiments of the subject invention, a mathematical model can be used to describe at a functional level:
  motor intent (intended movement and level of effort for that movement) generation in the nervous system;
  the functional connectivity between upper motor control circuitry of the nervous system and spinal cord motor neurons and motor pools (this is essentially the mapping between upper motor centers in the nervous system and spinal cord motor neurons;

translation of motor intent signals to neural firing by spinal cord motor neurons;

organization of spinal cord motor neurons into motor pools;

organization of motor pools axons into groups of motor axons;

neural interface electrodes recording processes;

functional connectivity between neural interface and spinal cord motor neurons and their axons (this is essentially the mapping of neural firings of spinal cord motor neurons to neural recording by neural interface electrodes);

effects of external stimulation on spinal cord motor neurons;

end effector response to neural activity;

interaction of anesthesia with motor neurons and/or axons in the peripheral nervous system;

muscle action as a result of activation by motor neurons; and/or effects of sensory inputs to spinal cord motor neurons.

In an embodiment, a system can include computer-readable medium having computer-executable instructions for performing one or more of the methods, mathematical models, and/or simulations disclosed herein. A simulation can be used to obtain physical results. The model or simulation can be operated in real-time and can be implemented in firmware (e.g., field-programmable gate array (FPGA), microcontroller) and/or specialized hardware (e.g., Very large Scale Integration (VLSI)).

In many embodiments, a mathematical model can simulate neural recordings for a variety of peripheral neural interfaces, such as point electrodes, longitudinal or transverse intrafascicular electrodes, CUFF electrodes, and multielectrode arrays that interface with peripheral nerves. The model can simulate EMG activity of muscles innervated by motor pools and/or the behavior of a variety of motor neurons (input-output response: threshold, saturation, and firing rates; spike characteristics: shape, duration, and amplitude). The model can also simulate a variety of electrode tissue interface characteristics, including but not limited to degree of encapsulation, different electrode impedances, and electrode drift. The model can simulate a variety of ambient noise in biological medium and in external environment and neural electrode interfaces.

In many embodiments, a mathematical model can implement a large variety of functional connectivity between motor intent generation centers and motor neurons of the spinal cord and/or can implement a large variety of functional connectivity between motor neurons and recording electrodes. The model can also implement a large variety of neural recoding conditions and can be used for rapid prototyping of neural interfaces.

In many embodiments, a mathematical model can simulate a variety of recording conditions such as level of ambient noise and recording systems characteristics, and/or can produce a large amount of data similar in nature to real neural data which can facilitate the development of neural decoding algorithms. The model can produce data sets to test hypotheses about motor control and interaction of the nervous system with neural interfaces, external stimuli, and sensory feedback. The model can also be used to simulate abnormal peripheral nerve recordings reflecting different neurological disorders (e.g., motor neuron diseases), and the resulting simulated signals can be analyzed and used to predict and classify possible causes of motor disorders (i.e., the model can be an aid in the diagnosis of neurological disorders).

Systems and methods of the subject invention can be used to convert voluntary motor intent to patterns of neural activity, as well as to convert involuntary motor output to patterns of neural activity in peripheral nerves. The ability of neural activity to control an end effector (e.g., a prosthetic limb) can be evaluated using embodiments of the subject invention. Mathematical models of the subject invention, which are used in conjunction with the systems and methods of the subject invention, can be used to design nerve stimulation protocols for interventions such as stimulation for regional anesthesia, partial paralysis, footdrop, gastric stimulation (gastroparesis), phrenic nerve stimulation (respiratory control), vagal nerve stimulation, and other peripheral nerves stimulation applications. Such models are easily configurable and scalable and can be used as a diagnostic tool. They can also be used for rapid testing of experimental paradigms and to test hypotheses in cases when real data is not available, thereby saving time and money that would have been spent in conducting real experiments. Rapid testing of neural decoding algorithms can also be performed.

Systems and methods of the subject invention facilitate research in motor control and spinal cord injury or motor neuron diseases (e.g., ALS). They can also be used to aid in studying the functional characteristics of neural recording electrodes, which can lead to a faster evaluation of recording electrode recording efficiency.

Systems and methods of the subject invention can be used for modeling and simulation of high level cognitive functions at the cortical level, including motor intent, motor movements and planning, and levels of sensation and perception. Also, spinal cord motor pools, pathways, and sensory nuclei pathways at a functional level can be modeled and simulated. Further, peripheral nerve structure and function, including motor axons and sensory axons, can be modeled and simulated. In addition, peripheral neural interfaces for recording or stimulation can be modeled and simulated.

Systems and methods of the subject invention can be used to: generate realistic neural recording scenarios; generate different neural stimulation scenarios; test and design decoding algorithms; test and design stimulation paradigms; simulate disease states of the spinal cord; and/or simulate malfunctions of peripheral interfaces (e.g., chemical, mechanical, and/or electrical).

The methods and processes described herein can be embodied as code and/or data. The software code and data described herein can be stored on one or more computer readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals.

EXAMPLES

Following are examples that illustrate procedures for practicing the invention. These examples should not be construed as limiting.

Example 1

Figure 6:
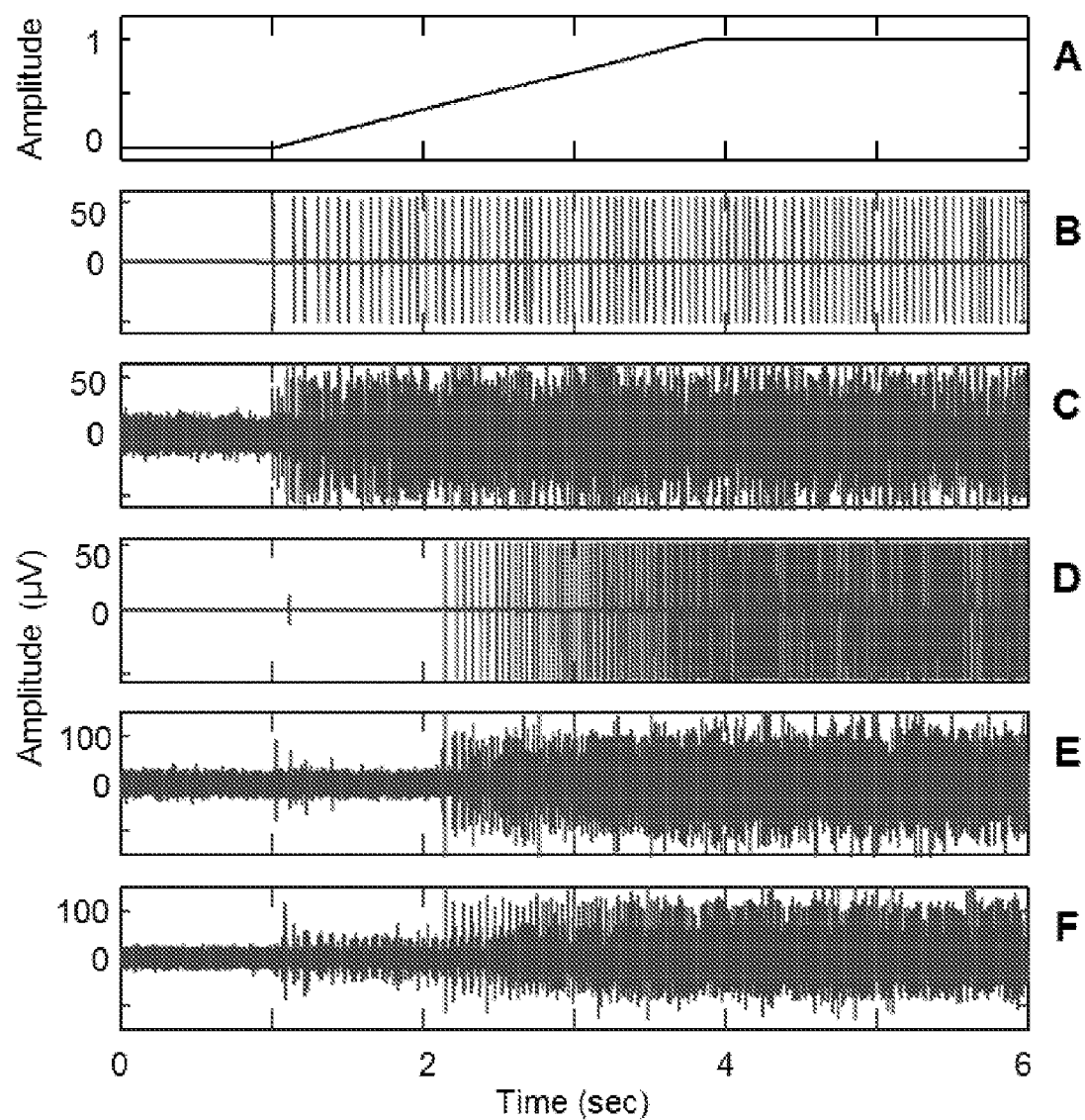
FIGS. 6A-F show simulated LIFE recordings.

FIG. 6 shows simulated LIFEs recordings from fast and slow motor neurons in response to a slow ramp and hold motor intent. Different motor axons contribute different firing patterns to a LIFE electrode recording. Slow motor neurons have sparse firing, longer spike duration and smaller amplitudes while fast fibers have larger amplitudes, shorter spikes, and denser firing patterns. A LIFE electrode, depending where it is placed in a nerve fascicle, could either pick activity from slow, fast, or a mix of motor axons. FIG. 6A is the motor intent signal, a ramp up to a maximum contraction. FIG. 6B is action potentials from a slow motor neuron, and FIG. 6C is a LIFE recording from axons of many slow motor neurons. FIG. 6D is firings of a fast motor neuron, and FIG. 6E is a LIFE recording from axons of fast motor neurons. FIG. 6F is a LIFE recording from a mixture of slow and fast motor neurons.

Example 2

Figure 7:
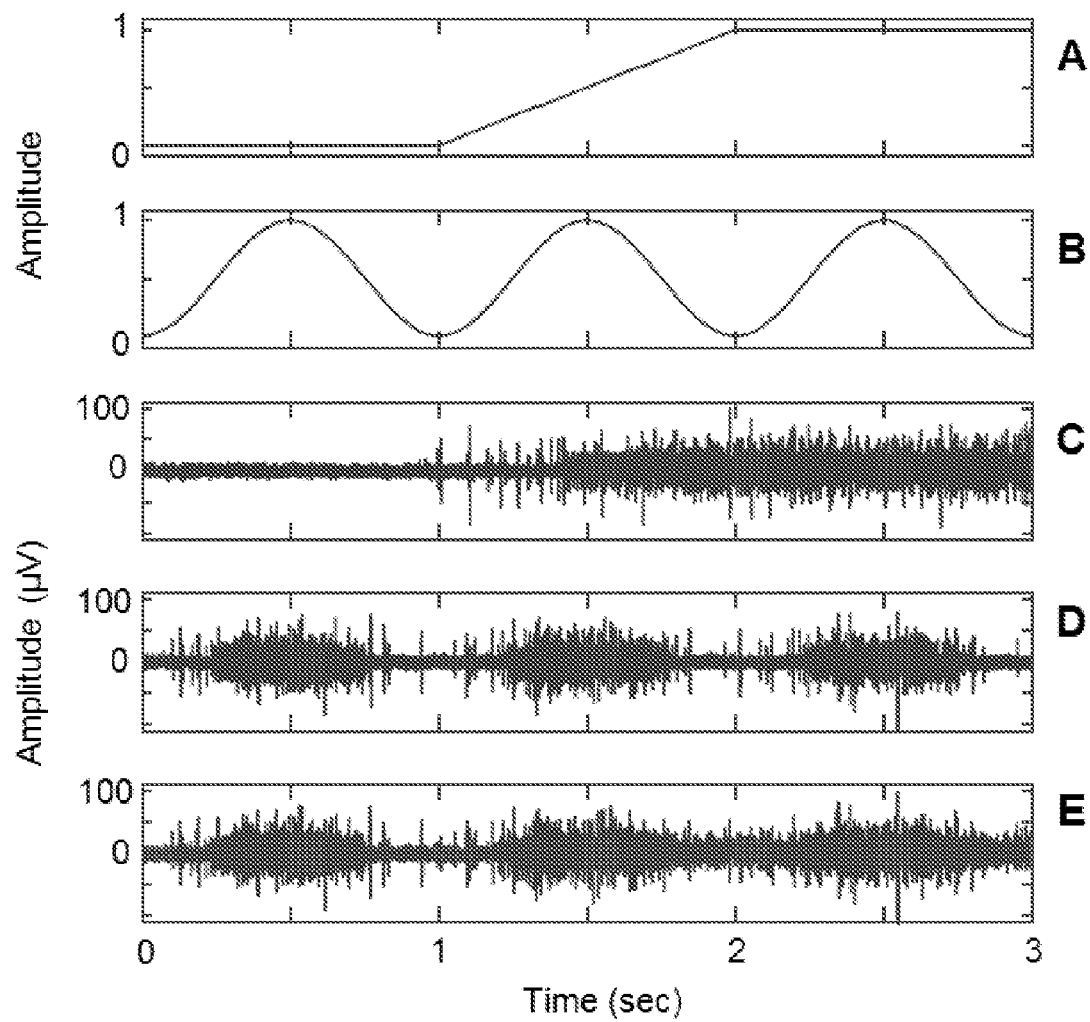
FIGS. 7A-E show simulated LIFE recordings.

FIG. 7 demonstrates the ability of the simulator to generate LIFEs recording for multiple degrees of freedom (DOF) tasks, in this case two DOF. FIG. 7A is motor intent pertaining to the 1st DOF, such as a grip and hold. FIG. 7B is motor intent pertaining to the 2nd DOF with a series of contractions and relaxations, for example, a bicep flexor. FIG. 7C is recording from a LIFE electrode situated in between motor axons associated with the first DOF motor intent, and FIG. 7D is a LIFE recording associated with the second DOF motor intent. FIG. 7E is neural recording from a LIFE electrode picking up signals from two motor pools associated with both the first and second DOFs.

Asymmetric spikes have a large and sharp positive peak but shallow and broad negative peak. A decoding algorithm that depends on a simple thresholding of positive peaks could perform differently under these conditions than one that depends on thresholding of negative peaks. It is possible that spikes of different shape-asymmetry can superimpose on a single electrode recording. A decoding algorithm must be robust to changes in spike shapes. Referring to FIGS. 3 and 4C, spikes generated by derivatives of a Gamma function are asymmetric.

Example 3

Figure 8:
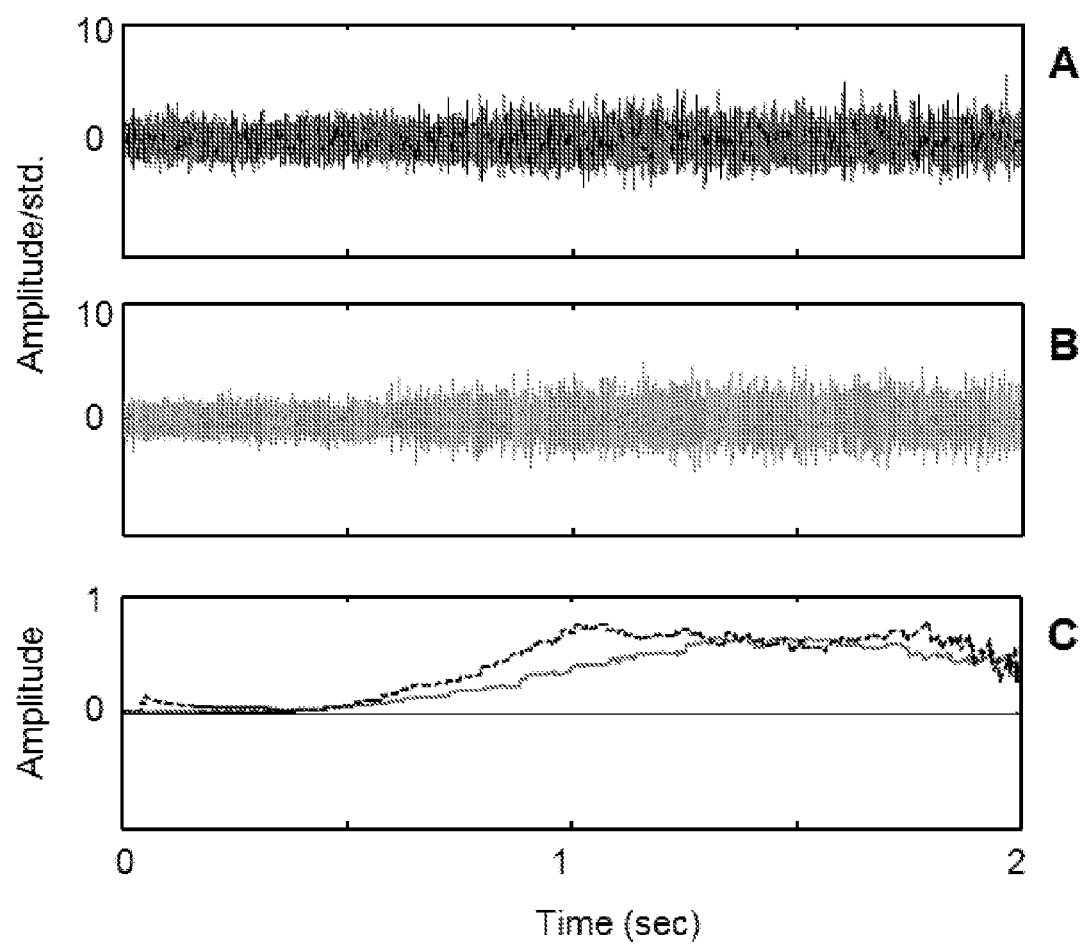
FIGS. 8A-C show a comparison of simulator data with LIFE-recorded data.

To demonstrate the ability of a simulator according to an embodiment of the subject invention to produce neural recordings that can mimic real neural recording, a simulated trace (from a simulator according to an embodiment of the subject invention) was compared to data acquired by a LIFE electrode (Dhillon, Lawrence et al. 2004; Dhillon and Horch 2005). First, the SNR ratio was set in the simulator to be equal to the SNR calculated from neural data. Second, motor intent was extracted using a simple moving average decoder from the real neural data. Then, a motor intent signal was produced that closely resembled the extracted motor intent in time and amplitude but was free of noise. This motor intent signal was used to generate the simulated neural data using symmetric spike shapes. FIG. 8 is a comparison of data from a LIFE simulator according to an embodiment of the subject invention with data recorded using a LIFE. The simulated data is shown in FIG. 8B, and experimental data is shown in FIG. 8A. Both simulated and experimental data were scaled using the standard deviation of the quiescent phase (i.e., a null motor intent). A moving-window (200 ms) sign-test between simulated and experimental data shows that they are not significantly different from each other (p≈1). FIG. 8C shows decoded motor intent; FIG. 8A shows the real recording from an actual LIFE, and FIG. 8B shows the simulated data.

FIG. 8C is the decoded motor intent signals from simulated and real data. This kind of comparison between simulated and real data is limited by the nature of the recorded neural data. Recorded neural data does not come with an independent measure of motor intent. Thus, the motor intent signal used to generate the simulated neural recording is the result of a simplified decoding scheme and estimation by an experienced person and is not a true representation of the original motor intent signal.

Example 4

Figure 9:
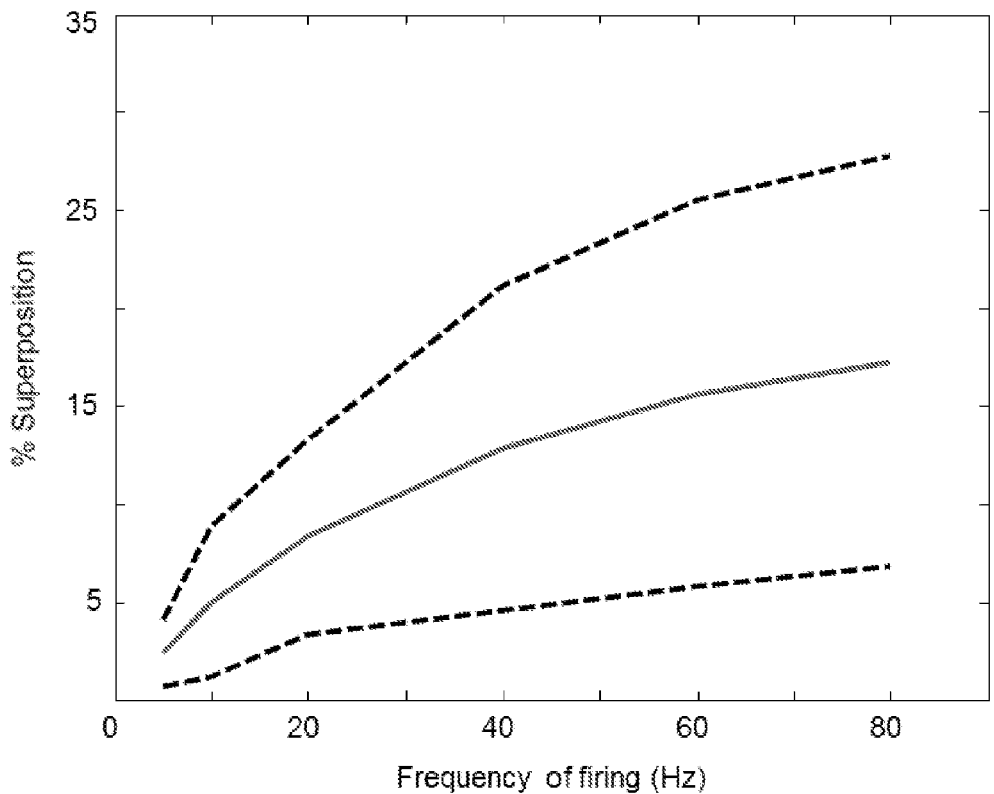
FIG. 9 shows a plot of percent superposition as a function of frequency of firing.

FIG. 9 presents estimations of the degree of superposition versus frequency of firing of motor neurons. This is relevant to the testing of decoding strategies. Percent superposition increases as a result of increased firing rate of motor neurons and the number of axons recorded from by the LIFEs. The standard deviation band is the result of other factors that influence the degree of superposition including spike shape and duration, type of neuron, and amount of crosstalk between electrodes. The solid line is the mean superposition, and the dashed lines represent the standard deviation band. Percent superposition increases as a result of increased firing rate of motor neurons and the number of axons recorded from by the LIFEs.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those listed in the References section) are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Allison, T., G. McCarthy, et al. (1992). "The relationship between human long-latency somatosensory evoked 1. potentials recorded from the cortical surface and from the scalp." *Electroencephalofr Clin Neurophysiol* 84(4): 301-314.
2. Ayaz, H., P. A. Shewokis, et al. (2011). "An optical brain computer interface for environmental control." *Conf Proc IEEE Eng Med Biol Soc* 2011: 6327-6330.
3. Bashor, D. P. (1998). "A large-scale model of some spinal reflex circuits." *Biological Cybernetics* 78(2): 147-157.
4. Blakely, T., K. J. Miller, et al. (2009). "Robust, long-term control of an electrocorticographic brain-computer interface with fixed parameters." *Neurosurg Focus* 27(1): E13.
5. Brand, O. (2005). *Cmos-Mems*. Weinheim, Wiley-VCH.
6. Branner, A. and R. A. Normann (2000). "A multielectrode array for intrafascicular recording and stimulation in sciatic nerve of cats." *Brain Research Bulletin* 51(4): 293-306.
7. Brown, S. P., W. C. Miller, et al. (2006). *Exercise physiology: basis of human movement in health and disease*. Philadelphia, Lippincott Williams & Wilkins.
8. Capaday, C. and R. B. Stein (1987). "A method for simulating the reflex output of a motoneuron pool." *J Neurosci Methods* 21(2-4): 91-104.
9. Carp, J. S. and J. R. Wolpaw (2001). Motor Neurons and Spinal Control of Movement. *eLS*, John Wiley & Sons, Ltd.
10. Cisi, R. R. and A. F. Kohn (2008). "Simulation system of spinal cord motor nuclei and associated nerves and muscles, in a Web-based architecture." *J Comput Neurosci* 25(3): 520-542.
11. Clark, G. A., N. M. Ledbetter, et al. (2011). "Recording sensory and motor information from peripheral nerves with Utah Slanted Electrode Arrays." *Conf Proc IEEE Eng Med Biol Soc* 2011: 4641-4644.
12. Dhillon, G. S. and K. W. Horch (2005). "Direct neural sensory feedback and control of a prosthetic arm." *IEEE Trans Neural Syst Rehabil Eng* 13(4): 468-472.
13. Dhillon, G. S., S. M. Lawrence, et al. (2004). "Residual function in peripheral nerve stumps of amputees: Implications for neural control of artificial limbs." *Journal of Hand Surgery-American Volume* 29A(4): 605-615.
14. Donoghue, J. P. (2002). "Connecting cortex to machines: recent advances in brain interfaces." *Nature Neuroscience* 5: 1085-1088.
15. Doud, A. J., J. P. Lucas, et al. (2011). "Continuous three-dimensional control of a virtual helicopter using a motor imagery based brain-computer interface." *PLoS One* 6(10): e26322.
16. Duran, C., N. Appleby, et al. (2009). "AutoSNPdb: an annotated single nucleotide polymorphism database for crop plants." *Nucleic Acids Res* 37(Database issue): D951-953.
17. Durand, D. M., H. J. Park, et al. (2008). "Localization and control of activity in peripheral nerves." *Conf Proc IEEE Eng Med Biol Soc* 2008: 3352-3354.
18. Fok, S., R. Schwartz, et al. (2011). "An EEG-based brain computer interface for rehabilitation and restoration of hand control following stroke using ipsilateral cortical physiology." *Conf Proc IEEE Eng Med Biol Soc* 2011: 6277-6280.
19. Fraser, G. W., S. M. Chase, et al. (2009). "Control of a brain-computer interface without spike sorting." *J Neural Eng* 6(5): 055004.
20. Halder, S., D. Agorastos, et al. (2011). "Neural mechanisms of brain-computer interface control." *Neuroimage* 55(4): 1779-1790.
21. Hallin, R. G. (1990). "Microneurography in relation to intraneural topography: somatotopic organisation of median nerve fascicles in humans." *J Neurol Neurosurg Psychiatry* 53(9): 736-744.
Henneman, E. and L. M. Mendell (2011). Functional Organization of Motoneuron Pool and its Inputs. *Comprehensive Physiology*, John Wiley & Sons, Inc.
22. Hochberg, L. R., D. Bacher, et al. (2012). "Reach and grasp by people with tetraplegia using a neurally controlled robotic arm." *Nature* 485(7398): 372-375.
23. Hochberg, L. R., M. D. Serruya, et al. (2006). "Neuronal ensemble control of prosthetic devices by a human with tetraplegia." *Nature* 442(7099): 164-171.
24. Hoffer, J. A. and G. E. Loeb (1980). "Implantable electrical and mechanical interfaces with nerve and muscle." *Ann Biomed Eng* 8(4-6): 351-360.
25. Horch, K. W. and G. S. Dhillon (2004). *Neuroprosthetics theory and practice*. River Edge, N.J., World Scientific.
26. Huang, D., K. Qian, et al. (2012). "Electroencephalography (EEG)-based brain-computer interface (BCI): a 2-D virtual wheelchair control based on event-related desynchronization/synchronization and state control." *IEEE Trans Neural Syst Rehabil Eng* 20(3): 379-388.
27. Ivashko, D. G., B. I. Prilutsky, et al. (2003). "Modeling the spinal cord neural circuitry controlling cat hindlimb movement during locomotion." *Neurocomputing* 52-4: 621-629.
28. Jankowska, E. (1992). "INTERNEURONAL RELAY IN SPINAL PATHWAYS FROM PROPRIOCEPTORS." *Progress in Neurobiology* 38(4): 335-378.
29. Kamavuako, E. N., W. Jensen, et al. (2010). "A criterion for signal-based selection of wavelets for denoising intrafascicular nerve recordings." *J Neurosci Methods* 186(2): 274-280.
30. Khokhar, Z. O., Z. G. Xiao, et al. (2010). "Surface EMG pattern recognition for real-time control of a wrist exoskeleton." *Biomed Eng Online* 9: 41.
31. Kreilinger, A., V. Kaiser, et al. (2011). "Switching between Manual Control and Brain-Computer Interface Using Long Term and Short Term Quality Measures." *Front Neurosci* 5: 147.
32. Krusienski, D. J. and J. J. Shih (2011). "Control of a brain-computer interface using stereotactic depth electrodes in and adjacent to the hippocampus." *J Neural Eng* 8(2): 025006.
33. Kuiken, T. A., G. Li, et al. (2009). "Targeted muscle reinnervation for real-time myoelectric control of multifunction artificial arms." *JAMA* 301(6): 619-628.
34. Lawrence, S. M., G. S. Dhillon, et al. (2004). "Acute peripheral nerve recording characteristics of polymer-based longitudinal intrafascicular electrodes." *Ieee Transactions on Neural Systems and Rehabilitation Engineering* 12(3): 345-348.
35. Lefurge, T., E. Goodall, et al. (1991). "Chronically implanted intrafascicular recording electrodes." *Ann Biomed Eng* 19(2): 197-207.
36. Long, J., Y. Li, et al. (2012). "A hybrid brain computer interface to control the direction and speed of a simulated or real wheelchair." *IEEE Trans Neural Syst Rehabil Eng* 20(5): 720-729.
37. Lowery, M. M. and Z. Erim (2005). "A simulation study to examine the effect of common motoneuron inputs on correlated patterns of motor unit discharge." *Journal of Computational Neuroscience* 19(2): 107-124.
38. Lynch, M. A. and S. M. O'Mara (1997). *Neuroscience labfax*. San Diego, Academic Press.

39. Malagodi, M. S., K. W. Horch, et al. (1989). "An intrafascicular electrode for recording of action potentials in peripheral nerves." *Ann Biomed Eng* 17(4): 397-410.
40. McKhann, G. M., 2nd (2008). "Cortical control of a prosthetic arm for self-feeding." *Neurosurgery* 63(2): N8-9.
41. Micera, S., X. Navarro, et al. (2008). "On the use of longitudinal intrafascicular peripheral interfaces for the control of cybernetic hand prostheses in amputees." *IEEE Trans Neural Syst Rehabil Eng* 16(5): 453-472.
42. Micera, S., P. M. Rossini, et al. (2011). "Decoding of grasping information from neural signals recorded using peripheral intrafascicular interfaces." *J Neuroeng Rehabil* 8: 53.
43. Nussbaumer, R. M., D. G. Ruegg, et al. (2002). "Computer simulation of the motoneuron pool-muscle complex. I. Input system and motoneuron pool." *Biological Cybernetics* 86(4): 317-333.
44. Onose, G., C. Grozea, et al. (2012). "On the feasibility of using motor imagery EEG-based brain-computer interface in chronic tetraplegics for assistive robotic arm control: a clinical test and long-term post-trial follow-up." *Spinal Cord* 50(8): 599-608.
45. Polikov, V. S., P. A. Tresco, et al. (2005). "Response of brain tissue to chronically implanted neural electrodes." *J Neurosci Methods* 148(1): 1-18.
46. Qiao, S., M. Torkamani-Azar, et al. (2012). "Stationary wavelet transform and higher order statistical analyses of intrafascicular nerve recordings." *J Neural Eng* 9(5): 056014.
47. Rehbaum, H., N. Jiang, et al. (2012). "Real time simultaneous and proportional control of multiple degrees of freedom from surface EMG: Preliminary results on subjects with limb deficiency." *Conf Proc IEEE Eng Med Biol Soc* 2012: 1346-1349.
48. Stienen, A. H., A. C. Schouten, et al. (2007). "Analysis of reflex modulation with a biologically realistic neural network." *J Comput Neurosci* 23(3): 333-348.
49. Subramanian, K., P. Okey, et al. (2005). "NVIZ: An integrated environment for simulation, visualization and analysis of spinal neuronal dynamics." *Journal of Imaging Science and Technology* 49(5): 505-519.
50. Tang, Y., B. Wodlinger, et al. (2011). "An algorithm for source signal extraction from the peripheral nerve." *Conf Proc IEEE Eng Med Biol Soc* 2011: 4251-4254.
51. Tyler, D. J. and D. M. Durand (2002). "Functionally selective peripheral nerve stimulation with a flat interface nerve electrode." *IEEE Trans Neural Syst Rehabil Eng* 10(4): 294-303.
52. Uchiyama, T. and U. Windhorst (2007). "Effects of spinal recurrent inhibition on motoneuron short-term Allison, T., G. McCarthy, et al. (1992). "The relationship between human long-latency somatosensory evoked potentials recorded from the cortical surface and from the scalp." *Electroencephalogr Clin Neurophysiol* 84(4): 301-314.
53. Ayaz, H., P. A. Shewokis, et al. (2011). "An optical brain computer interface for environmental control." *Conf Proc IEEE Eng Med Biol Soc* 2011: 6327-6330.
54. Bashor, D. P. (1998). "A large-scale model of some spinal reflex circuits." *Biological Cybernetics* 78(2): 147-157.
55. Blakely, T., K. J. Miller, et al. (2009). "Robust, long-term control of an electrocorticographic brain-computer interface with fixed parameters." *Neurosurg Focus* 27(1): E13.
56. Brand, O. (2005). *Cmos-Mems*. Weinheim, Wiley-VCH.
57. Branner, A. and R. A. Normann (2000). "A multielectrode array for intrafascicular recording and stimulation in sciatic nerve of cats." *Brain Research Bulletin* 51(4): 293-306.
58. Brown, S. P., W. C. Miller, et al. (2006). *Exercise physiology: basis of human movement in health and disease.* Philadelphia, Lippincott Williams & Wilkins.
59. Capaday, C. and R. B. Stein (1987). "A method for simulating the reflex output of a motoneuron pool." *J Neurosci Methods* 21(2-4): 91-104.
60. Carp, J. S. and J. R. Wolpaw (2001). Motor Neurons and Spinal Control of Movement. *eLS*, John Wiley & Sons, Ltd.
61. Cisi, R. R. and A. F. Kohn (2008). "Simulation system of spinal cord motor nuclei and associated nerves and muscles, in a Web-based architecture." *J Comput Neurosci* 25(3): 520-542.
62. Clark, G. A., N. M. Ledbetter, et al. (2011). "Recording sensory and motor information from peripheral nerves with Utah Slanted Electrode Arrays." *Conf Proc IEEE Eng Med Biol Soc* 2011: 4641-4644.
63. Dhillon, G. S. and K. W. Horch (2005). "Direct neural sensory feedback and control of a prosthetic arm." *IEEE Trans Neural Syst Rehabil Eng* 13(4): 468-472.
64. Dhillon, G. S., S. M. Lawrence, et al. (2004). "Residual function in peripheral nerve stumps of amputees: Implications for neural control of artificial limbs." *Journal of Hand Surgery-American Volume* 29A(4): 605-615.
65. Donoghue, J. P. (2002). "Connecting cortex to machines: recent advances in brain interfaces." *Nature Neuroscience* 5: 1085-1088.
66. Doud, A. J., J. P. Lucas, et al. (2011). "Continuous three-dimensional control of a virtual helicopter using a motor imagery based brain-computer interface." *PLoS One* 6(10): e26322.
67. Duran, C., N. Appleby, et al. (2009). "AutoSNPdb: an annotated single nucleotide polymorphism database for crop plants." *Nucleic Acids Res* 37(Database issue): n951-953.
68. Durand, D. M., H. J. Park, et al. (2008). "Localization and control of activity in peripheral nerves." *Conf Proc IEEE Eng Med Biol Soc* 2008: 3352-3354.
69. Fok, S., R. Schwartz, et al. (2011). "An EEG-based brain computer interface for rehabilitation and restoration of hand control following stroke using ipsilateral cortical physiology." *Conf Proc IEEE Eng Med Biol Soc* 2011: 6277-6280.
70. Fraser, G. W., S. M. Chase, et al. (2009). "Control of a brain-computer interface without spike sorting." *J Neural Eng* 6(5): 055004.
71. Halder, S., D. Agorastos, et al. (2011). "Neural mechanisms of brain-computer interface control." *Neuroimage* 55(4): 1779-1790.
72. Hallin, R. G. (1990). "Microneurography in relation to intraneural topography: somatotopic organisation of median nerve fascicles in humans." *J Neurol Neurosurg Psychiatry* 53(9): 736-744.
73. Henneman, E. and L. M. Mendell (2011). Functional Organization of Motoneuron Pool and its Inputs. *Comprehensive Physiology*, John Wiley & Sons, Inc.
74. Hochberg, L. R., D. Bacher, et al. (2012). "Reach and grasp by people with tetraplegia using a neurally controlled robotic arm." *Nature* 485(7398): 372-375.
75. Hochberg, L. R., M. D. Serruya, et al. (2006). "Neuronal ensemble control of prosthetic devices by a human with tetraplegia." *Nature* 442(7099): 164-171.

76. Hoffer, J. A. and G. E. Loeb (1980). "Implantable electrical and mechanical interfaces with nerve and muscle." *Ann Biomed Eng* 8(4-6): 351-360.
77. Horch, K. W, and G. S. Dhillon (2004). *Neuroprosthetics theory and practice*. River Edge, N.J., World Scientific.
78. Huang, D., K. Qian, et al. (2012). "Electroencephalography (EEG)-based brain-computer interface (BCI): a 2-D virtual wheelchair control based on event-related desynchronization/synchronization and state control." *IEEE Trans Neural Syst Rehabil Eng* 20(3): 379-388.
79. Ivashko, D. G., B. I. Prilutsky, et al. (2003). "Modeling the spinal cord neural circuitry controlling cat hindlimb movement during locomotion." *Neurocomputing* 52-4: 621-629.
80. Jankowska, E. (1992). "Interneuronal Relay in Spinal Pathways from Proprioceptors." *Progress in Neurobiology* 38(4): 335-378.
81. Kamavuako, E. N., W. Jensen, et al. (2010). "A criterion for signal-based selection of wavelets for denoising intrafascicular nerve recordings." *J Neurosci Methods* 186(2): 274-280.
82. Khokhar, Z. O., Z. G. Xiao, et al. (2010). "Surface EMG pattern recognition for real-time control of a wrist exoskeleton." *Biomed Eng Online* 9: 41.
83. Kreilinger, A., V. Kaiser, et al. (2011). "Switching between Manual Control and Brain-Computer Interface Using Long Term and Short Term Quality Measures." *Front Neurosci* 5: 147.
84. Krusienski, D. J. and J. J. Shih (2011). "Control of a brain-computer interface using stereotactic depth electrodes in and adjacent to the hippocampus." *J Neural Eng* 8(2): 025006.
85. Kuiken, T. A., G. Li, et al. (2009). "Targeted muscle reinnervation for real-time myoelectric control of multifunction artificial arms." *JAMA* 301(6): 619-628.
86. Lawrence, S. M., G. S. Dhillon, et al. (2004). "Acute peripheral nerve recording characteristics of polymer-based longitudinal intrafascicular electrodes." *Ieee Transactions on Neural Systems and Rehabilitation Engineering* 12(3): 345-348.
87. Lefurge, T., E. Goodall, et al. (1991). "Chronically implanted intrafascicular recording electrodes." *Ann Biomed Eng* 19(2): 197-207.
88. Long, J., Y. Li, et al. (2012). "A hybrid brain computer interface to control the direction and speed of a simulated or real wheelchair" *IEEE Trans Neural Syst Rehabil Eng* 20(5): 720-729.
89. Lowery, M. M. and Z. Erim (2005). "A simulation study to examine the effect of common motoneuron inputs on correlated patterns of motor unit discharge." *Journal of Computational Neuroscience* 19(2): 107-124.
90. Lynch, M. A. and S. M. O'Mara (1997). *Neuroscience labfax*. San Diego, Academic Press.
91. Malagodi, M. S., K. W. Horch, et al. (1989). "An intrafascicular electrode for recording of action potentials in peripheral nerves." *Ann Biomed Eng* 17(4): 397-410.
92. McKhann, G. M., 2nd (2008). "Cortical control of a prosthetic arm for self-feeding." *Neurosurgery* 63(2): N8-9.
93. Micera, S., X. Navarro, et al. (2008). "On the use of longitudinal intrafascicular peripheral interfaces for the control of cybernetic hand prostheses in amputees." *IEEE Trans Neural Syst Rehabil Eng* 16(5): 453-472.
94. Micera, S., P. M. Rossini, et al. (2011). "Decoding of grasping information from neural signals recorded using peripheral intrafascicular interfaces." *J Neuroeng Rehabil* 8: 53.
95. Nussbaumer, R. M., D. G. Ruegg, et al. (2002). "Computer simulation of the motoneuron pool-muscle complex. I. Input system and motoneuron pool." *Biological Cybernetics* 86(4): 317-333.
96. Onose, G., C. Grozea, et al. (2012). "On the feasibility of using motor imagery EEG-based brain-computer interface in chronic tetraplegics for assistive robotic arm control: a clinical test and long-term post-trial follow-up." *Spinal Cord* 50(8): 599-608.
97. Polikov, V. S., P. A. Tresco, et al. (2005). "Response of brain tissue to chronically implanted neural electrodes." *J Neurosci Methods* 148(1): 1-18.
98. Qiao, S., M. Torkamani-Azar, et al. (2012). "Stationary wavelet transform and higher order statistical analyses of intrafascicular nerve recordings." *J Neural Eng* 9(5): 056014.
99. Rehbaum, H., N. Jiang, et al. (2012). "Real time simultaneous and proportional control of multiple degrees of freedom from surface EMG: Preliminary results on subjects with limb deficiency." *Conf Proc IEEE Eng Med Biol Soc* 2012: 1346-1349.
100. Stienen, A. H., A. C. Schouten, et al. (2007). "Analysis of reflex modulation with a biologically realistic neural network." *J Comput Neurosci* 23(3): 333-348.
101. Subramanian, K., P. Okey, et al. (2005). "NVIZ: An integrated environment for simulation, visualization and analysis of spinal neuronal dynamics." *Journal of Imaging Science and Technology* 49(5): 505-519.
102. Tang, Y., B. Wodlinger, et al. (2011). "An algorithm for source signal extraction from the peripheral nerve." *Conf Proc IEEE Eng Med Biol Soc* 2011: 4251-4254.
103. Tyler, D. J. and D. M. Durand (2002). "Functionally selective peripheral nerve stimulation with a flat interface nerve electrode." *IEEE Trans Neural Syst Rehabil Eng* 10(4): 294-303.
104. Uchiyama, T. and U. Windhorst (2007). "Effects of spinal recurrent inhibition on motoneuron short-term synchronization." *Biol Cybern* 96(6): 561-575.
105. Velliste, M., S. Perel, et al. (2008). "Cortical control of a prosthetic arm for self-feeding." *Nature* 453(7198): 1098-1101.
106. Veraart, C., W. M. Grill, et al. (1993). "Selective control of muscle activation with a multipolar nerve cuff electrode." *IEEE Trans Biomed Eng* 40(7): 640-653.
107. Wang, P. T., C. E. King, et al. (2012). "Self-paced brain-computer interface control of ambulation in a virtual reality environment." *J Neural Eng* 9(5): 056016.
108. Wodlinger, B. (January, 2011). *Extracting Command Signals from Peripheral Nerve Recordings*, Doctor of Philosophy, Case Western Reserve University.
109. Wodlinger, B. and D. M. Durand (2011). "Recovery of neural activity from nerve cuff electrodes." *Conf Proc IEEE Eng Med Biol Soc* 2011: 4653-4656.
110. Wolpaw, J. R., D. J. McFarland, et al. (1991). "An EEG-based brain-computer interface for cursor control." *Electroencephalogr Clin Neurophysiol* 78(3): 252-259.
111. Wood, F., M. Fellows, et al. (2004). "Automatic spike sorting for neural decoding." *Conf Proc IEEE Eng Med Biol Soc* 6: 4009-4012.
112. Yoshida, K., D. Pellinen, et al. (2000). *Development of the thin-film longitudinal intra-fascicular electrode*. Proceedings of the fifth Annual Conf. of the IFESS.
113. Zhou, R., N. Jiang, et al. (2010). "A computational model and simulation study of the efferent activity in the brachial nerves during voluntary motor intent." *Med Biol Eng Comput* 48(1): 67-77.

114. Zhu, X., C. Guan, et al. (2005). "Bayesian Method for Continuous Cursor Control in EEG-Based Brain-Computer Interface." *Conf Proc IEEE Eng Med Biol Soc* 7: 7052-7055.

What is claimed is:

1. A system comprising a non-transitory machine-readable medium having computer-executable instructions for performing a method to simulate activity recorded from an interface to nerve fibers, the method comprising:
   simulating generation of at least one signal of a variable capable of being recorded by an interface to nerve fibers;
   simulating translation of the variable to motor neuron firing;
   generating a realistic simulated neural recording that corresponds to how a real body would respond to motor neuron stimulus of the nerve fibers; and
   simulating recording of the motor neuron firing by the interface to nerve fibers,
   wherein the simulated activity is neural activity, and
   wherein simulating recording of the motor neuron firing comprises:
      generating a virtual electrode;
      mapping the motor neuron firing to signals of the virtual electrode by a mapping matrix B; and
      multiplying a cross-talk matrix C and the mapping matrix B.

2. The system according to claim 1,
   wherein the variable is motor intent, and
   wherein the interface to nerve fibers is a peripheral neural interface.

3. The system according to claim 1, wherein the method to simulate neural activity is performed by a mathematical model.

4. The system according to claim 3, wherein the mathematical model comprises a motor intent generation unit, a motor pools unit, and an electrode function unit,
   wherein the motor intent generation unit simulates the generation of at least one motor intent signal,
   wherein the motor pools unit simulates the translation of motor intent to motor neuron firing, and
   wherein the electrode function unit simulates the recording of the motor neuron firing.

5. The system according to claim 1, wherein simulating recording of the motor neuron firing comprises simulating recording of the motor neuron firing by at least one longitudinal intrafascicular electrode (LIFE).

6. The system according to claim 1, wherein the steps of the method to simulate activity recorded from an interface to nerve fibers are initiated by a user of the system, and wherein the user initiates the steps using a command prompt of the system.

7. The system according to claim 1, further comprising a graphical user interface (GUI), wherein the steps of the method to simulate activity recorded from an interface to nerve fibers are initiated by a user of the system, and wherein the user initiates the steps using the GUI.

8. The system according to claim 1, wherein the non-transitory machine-readable medium comprises firmware, and wherein the firmware comprises the computer-executable instructions.

9. The system according to claim 1, wherein the method to simulate activity recorded from an interface to nerve fibers further comprises simulating at least one spike template,
   wherein a user of the system simulates the at least one spike template, and
   wherein simulating the at least one spike template comprises:
      selecting, by the user, at least one normalized spike morphology; and
      selecting, by the user, a characteristic of the spike template, wherein the characteristic is selected from the group consisting of: neuron type; axon size and myelination; shape and distance of a recording electrode from an axon; and degree and type of encapsulation around the recording electrode.

10. The system according to claim 9, wherein simulating the at least one spike template further comprises scaling the at least one spike template after selecting, by the user, the characteristic of the spike template.

11. The system according to claim 2, wherein simulating translation of motor intent to motor neuron firing comprises simulation of motor pool activity of a spinal cord.

12. A method of simulating activity recorded from an interface to nerve fibers, comprising:
   simulating, by a system comprising a non-transitory machine-readable medium, generation of at least one signal of a variable capable of being recorded by an interface to nerve fibers;
   simulating translation of the variable to motor neuron firing;
   generating a realistic simulated neural recording that corresponds to how a real body would respond to motor neuron stimulus of the nerve fibers; and
   simulating recording of the motor neuron firing by the interface to nerve fibers,
   wherein the simulated activity is neural activity, and
   wherein the simulating recording of the motor neuron firing comprises:
      generating a virtual electrode;
      mapping the motor neuron firing, to signals of the virtual electrode by a mapping matrix B; and
      multiplying a cross-talk matrix C and the mapping matrix B.

13. The method according to claim 12,
   wherein the variable is motor intent, and
   wherein the interface to nerve fibers is a peripheral neural interface.

14. The method according to claim 12, wherein the non-transitory machine-readable medium comprises a mathematical model.

15. The method according to claim 14, wherein the mathematical model comprises a motor intent generation unit, a motor pools unit, and an electrode function unit,
   wherein the motor intent generation unit simulates the generation of at least one motor intent signal,
   wherein the motor pools unit simulates the translation of motor intent to motor neuron firing, and
   wherein the electrode function unit simulates the recording of the motor neuron firing.

16. The method according to claim 12, wherein simulating recording of the motor neuron firing comprises simulating recording of the motor neuron firing by at least one longitudinal intrafascicular electrode (LIFE).

17. The method according to claim 12, wherein the steps of the method to simulate activity recorded from an interface to nerve fibers are initiated by a user of the system, and
   wherein the user initiates the steps using a graphical user interface (GUI) of the system.

18. The method according to claim 12, further comprising simulating at least one spike template,
   wherein a user of the system simulates the at least one spike template, and wherein simulating the at least one spike template comprises:
  selecting, by the user, at least one normalized spike morphology; and
  selecting, by the user, a characteristic of the spike template, wherein the characteristic is selected from the group consisting of: neuron type; axon size and myelination; shape and distance of a recording electrode from an axon; and degree and type of encapsulation around the recording electrode.

19. The method according to claim 18, wherein simulating the at least one spike template further comprises scaling the at least one spike template after selecting, by the user, the characteristic of the spike template.

20. The method according to claim 13, wherein simulating translation of motor intent to motor neuron firing comprises simulation of motor pool activity of a spinal cord.

21. A system comprising a graphical user interface (GUI) and a non-transitory machine-readable medium having computer-executable instructions for performing a method to simulate neural activity recorded from an interface to nerve fibers using a mathematical model that comprises a motor intent generation unit that simulates the generation of at least one motor intent signal, a motor pools unit that simulates the translation of motor intent to motor neuron firing, and an electrode function unit that simulates the recording of the motor neuron firing, the method comprising:
  simulating, by a user using the GUI, generation of at least one signal of motor intent that is capable of being recorded by a peripheral neural interface to nerve fibers;
  simulating translation of motor intent to motor neuron firing by simulating motor pool activity of a spinal cord;
  generating a realistic simulated neural recording that corresponds to how a real body would respond to motor neuron stimulus of the nerve fibers;
  simulating recording of the motor neuron firing by the interface to nerve fibers; and
  simulating, by the user, at least one spike template by:
    selecting, by the user, at least one normalized spike morphology;
    selecting, by the user, a characteristic of the spike template, selected from the group consisting of: neuron type; axon size and myelination; shape and distance of a recording electrode from an axon; and degree and type of encapsulation around the recording electrode; and
    scaling the at least one spike template after selecting the characteristic of the spike template,
  wherein the simulating recording of the motor neuron firing comprises:
    generating a virtual electrode;
    mapping the motor neuron firing to signals of the virtual electrode by a mapping matrix B; and
    multiplying a cross-talk matrix C and the mapping matrix B.

* * * * *

UNITED STATES PATENT AND TRADEMARK OFFICE
CERTIFICATE OF CORRECTION

PATENT NO. : 9,563,740 B2  
APPLICATION NO. : 14/385905  
DATED : February 7, 2017  
INVENTOR(S) : Mohamed Abdelghani et al.

Page 1 of 1

It is certified that error appears in the above-identified patent and that said Letters Patent is hereby corrected as shown below:

In the Specification

Column 3,  
Line 48, "device" should read --drive--.

Column 8,  
Line 26, "x toy" should read --$x$ to $y$--.

Column 11,  
Line 14, "where H is an lxm" should read --where $B$ is an $l \times m$--.

Signed and Sealed this  
Thirteenth Day of March, 2018

Andrei Iancu  
*Director of the United States Patent and Trademark Office*